United States Patent
Iseki et al.

(10) Patent No.: US 8,222,617 B2
(45) Date of Patent: Jul. 17, 2012

(54) LASER-DRIVEN PARTICLE BEAM IRRADIATION APPARATUS AND METHOD

(75) Inventors: Yasushi Iseki, Yokohama (JP); Takeshi Yoshiyuki, Yokohama (JP); Hiroyuki Daido, Takatsuki (JP); Masahiro Ikegami, Nara (JP); Mamiko Nishiuchi, Kizukawa (JP); Akira Noda, Kyoto (JP)

(73) Assignees: Kabushiki Kaisha Toshiba, Tokyo (JP); Japan Atomic Energy Agency, Naka-Gun (JP)

( * ) Notice: Subject to any disclaimer, the term of this patent is extended or adjusted under 35 U.S.C. 154(b) by 474 days.

(21) Appl. No.: 12/509,116

(22) Filed: Jul. 24, 2009

(65) Prior Publication Data
US 2010/0127183 A1   May 27, 2010

(30) Foreign Application Priority Data
Nov. 26, 2008   (JP) ................. P2008-301695

(51) Int. Cl.
*G21G 5/00* (2006.01)
(52) U.S. Cl. .............. 250/492.1; 250/492.2; 250/423 R; 250/396 R; 250/396 ML
(58) Field of Classification Search ............... 250/492.1, 250/492.2, 423 R, 396 R, 396 ML
See application file for complete search history.

(56) References Cited

U.S. PATENT DOCUMENTS

| | | | | |
|---|---|---|---|---|
| 6,744,225 B2 * | 6/2004 | Okamura et al. | ............. | 315/505 |
| 2005/0029471 A1 * | 2/2005 | Kraft et al. | ................. | 250/492.1 |
| 2006/0145088 A1 * | 7/2006 | Ma | ......................... | 250/396 ML |
| 2006/0231775 A1 * | 10/2006 | Harada | ....................... | 250/492.3 |
| 2008/0191143 A1 * | 8/2008 | Willi et al. | ............. | 250/396 ML |

* cited by examiner

*Primary Examiner* — Michael Maskell
(74) *Attorney, Agent, or Firm* — Oblon, Spivak, McClelland, Maier & Neustadt, L.L.P.

(57) ABSTRACT

A laser-driven particle beam irradiation apparatus includes: a particle beam generator irradiating a target with pulsed laser light to emit a laser-driven particle ray; a beam converging unit forming a transportation path which guides the emitted laser-driven particle ray to an object and spatially converging the laser-driven particle ray; an energy selector selecting an energy and an energy width of the laser-driven particle ray; an irradiation port causing the laser-driven particle ray to scan the object to adjust an irradiation position in the object; and an irradiation controller controlling operation of the particle beam generator, the beam converging unit, the energy selector and the irradiation port. The beam converging unit generates a magnetic field on a trajectory of the laser-driven particle ray and converging the laser-driven particle ray by the magnetic field, the magnetic field forcing divergence components of the laser-driven particle ray that go away from a center of the trajectory back to the center of the trajectory.

6 Claims, 11 Drawing Sheets

| 001 | 002 | 003 | 004 | 005 | 006 |
|---|---|---|---|---|---|
| IRRADIATION POSITION (RELATIVE HORIZONTAL POSITION) | IRRADIATION POSITION (RELATIVE VERTICAL POSITION) | RANGE IN PATIENT (mm) | BEAM STOP POSITION WIDTH IN DEPTH (mm) | BEAM INTENSITY (Gy) | SET DOSE (Gy) |
| 4 | 8 | 156 | 5.0 | 682 | 769 |
| 2 | 8 | 156 | 5.0 | 682 | 2312 |
| 0 | 8 | 156 | 5.0 | 682 | 1544 |
| −2 | 8 | 156 | 5.0 | 682 | 1983 |
| −4 | 6 | 156 | 5.0 | 682 | 593 |
| −2 | 6 | 156 | 5.0 | 682 | 324 |
| 0 | 6 | 156 | 5.0 | 682 | 1237 |
| ⋮ | ⋮ | ⋮ | ⋮ | ⋮ | ⋮ |
| 6 | 8 | 100 | 5.0 | 983 | 683 |
| 4 | 8 | 100 | 5.0 | 983 | 239 |
| 2 | 8 | 100 | 5.0 | 983 | 425 |

LASER-DRIVEN PARTICLE BEAM IRRADIATION APPARATUS AND METHOD

BACKGROUND OF THE INVENTION

1. Field of the Invention

The present invention relates to a laser-driven particle beam irradiation technology in which a target is irradiated with pulsed laser light to extract laser-driven particle rays and to use the laser-driven particle rays as irradiation particle rays used for analysis or other purposes and, in particular, to a laser-driven particle beam irradiation apparatus and also relates to a laser-driven particle beam irradiation method that controls spatial distribution and energy distribution of laser-driven particle rays while transporting the laser-driven particle ray to an object to be irradiated.

2. Description of the Related Art

There has been proposed a particle beam irradiation technique that uses an accelerator such as a synchrotron to accelerate protons or charged particles of a substance such as carbon to produce an accelerated particle beam and brings the accelerated particle beam to rest in the body of a patient to kill cancer cells (see Patent Document 1: Japanese Patent Laid-Open Publication No. 2006-341069). Such an accelerator-driven particle beam irradiation technique requires a large accelerator facility which occupies a large installation space and involves much cost for installation or maintenance. Therefore, in recent technologies, widespread use has been prohibited and the technique has been used only in a limited number of facilities.

In light of these circumstances, a laser-driven proton beam irradiation technique has been envisioned in recent years (see Patent Documents 2 and 3: Japanese Patent Laid-Open Publications No. 2007-531556 and No. 2008-022994). The laser-driven proton beam irradiation technique irradiates a cancerous portion of a patient, for example, with a proton ray extracted by irradiating a metal or polymer thin film with high-intensity and ultrashort-pulse laser light (hereinafter referred to as laser-driven proton ray). The use of laser-driven proton rays will eliminate the need for a large accelerator facility and reduce equipment in size and cost, which can lead to wider use of proton irradiation technology such as proton radiation therapy.

Laser-driven proton rays have the property of being emitted from a target at a divergence angle and spatially spreading. Therefore, when laser-driven proton rays are used for therapy radiation, the exposed dose in normal tissue surrounding a diseased site should be reduced. That is, an operation is required for converging the laser-driven proton rays in the course of transportation of the laser-driven proton rays to the diseased site.

Since the laser-driven proton rays are emitted from the target at a diversion angle, the intensity of the rays tends to deteriorate in the course of transportation to the diseased site. The deterioration of the intensity of the laser-driven proton rays makes it impossible to use the laser-driven proton rays for therapy radiation or increases the irradiation time, which may result in the burden on the patient maintained in a fixed position and posture.

SUMMARY OF THE INVENTION

The present invention has been made in consideration of the circumstances mentioned above and an object of the present invention is to provide a laser-driven particle beam irradiation apparatus and a laser-driven particle beam irradiation method capable of performing therapy radiation using laser-driven particle rays and increasing the convergence of laser-driven particle rays while reducing deterioration of the intensity of the laser-driven particle rays in the course of transportation of the laser-driven particle rays to a diseased site of a patient.

The above and other objects can be achieved according to the present invention by providing, in one aspect, a laser-driven particle beam irradiation apparatus comprising:

a particle beam generator irradiating a target with pulsed laser light to emit a laser-driven particle ray;

a beam converging unit forming a transportation path which guides the emitted laser-driven particle ray to an object to be irradiated and spatially converging the laser-driven particle ray;

an energy selector selecting an energy and an energy width of the laser-driven particle ray;

an irradiation port causing the laser-driven particle ray to scan the object to be irradiated to adjust an irradiation position in the object; and an irradiation controller controlling operation of the particle beam generator, the beam converging unit, the energy selector, and the irradiation port;

wherein the beam converging unit generates a magnetic field on a trajectory of the laser-driven particle ray and converging the laser-driven particle ray by the magnetic field, the magnetic field forcing divergence components of the laser-driven particle ray that go away from a center of the trajectory back to the center of the trajectory.

In this aspect, the following embodiments or modes may be adopted.

The beam converging unit may be provided between the particle beam generator and the energy selector.

The beam converging unit may include a multipole magnet made of a permanent magnet and the multipole magnet generates the magnetic field. A plurality of the multipole magnets are provided along a transportation path of the laser-driven particle ray of the beam converging unit and at least one of the multiple magnets is provided to be movable.

The beam converging unit may include an angle collimator provided between the multipole magnets and the target of the particle beam generator and blocking wide-angle components of the laser-driven particle ray from reaching the multipole magnets.

The energy selector may be configured to generate, in the transportation path of laser-driven particle rays, a magnetic field deflecting laser-driven particle rays according to momentums thereof, select a laser-driven particle ray having a particular trajectory and remove remaining laser-drive particle rays from the transportation path so as to select laser-driven particle ray energy and energy width.

The energy selector may be provided with an electromagnet generating a variable magnetic field under control of an exciting current and an energy collimator provided so as to block the transportation path of a laser-driven particle lay deflected by the variable magnetic field and forming a slit selectively allowing a laser-driven particle ray having a particular trajectory to pass through the slit. It may be desired that the energy collimator of the energy selector adjusts a size of the slit.

The laser-driven particle beam irradiation apparatus may further include an energy distribution converging unit forming the transportation path of the laser-driven particle ray and converging an energy distribution of the laser-driven particle ray through the transportation path to provide a peak at a particular energy.

The energy distribution converging unit may include a phase rotation cavity unit forming a transportation path of the laser-driven particle ray and, under application of a high-frequency voltage, generating in the transportation path a high-frequency electric field in which a state in which protons in a bunch are accelerated and a state in which protons in a bunch are decelerated appear to converge the energy distribution of the laser-driven proton ray to a particular energy, and wherein the irradiation controller adjusts the phase of the high-frequency voltage to be applied to the phase rotation cavity unit to adjust the position of the energy peak of the energy distribution of the laser-driven particle ray.

The phase rotation cavity unit of the energy distribution converging unit may include an outer cavity forming the transportation path of the laser-driven particle ray and a plurality of inner cavities which are spaced in a row in the outer cavity and to which a high-frequency voltage is applied, wherein a high-frequency electric field is formed in a gap between adjacent inner cavities to converge the energy distribution of a proton beam around the energy of protons that enter the gap at a timing of being synchronized with the phase of the high-frequency voltage applied to the inner cavities among the protons in a bunch in the outer cavity.

It may be desired that the irradiation controller applies a pulse width compressing voltage to the inner cavities of the energy distribution converging unit to generate a high-frequency electric field in the gap between adjacent inner cavities, the pulse width compressing voltage being defined as $$V > \frac{E_0 \beta_0^2 \gamma_0^2}{q} \cdot \frac{\sqrt{1 - m^2 c^4 / E_0^2}}{\sqrt{1 - m^2 c^4 / E_0^2} + fL/c}$$

wherein f is the frequency of the high-frequency voltage to be applied to the inner cavities, L is the distance from a laser-driven particle ray emission point in the target to the gap between adjacent inner cavities, $\beta_0$ and $\gamma_0$ are Lorentz factors, $E_0$ is the total energy of the laser-driven particle ray, c is the speed of light, m is the mass of the laser-driven-particle ray, and q is the charge of the laser-driven particle ray.

The energy distribution converging unit may be provided between the beam converging unit and the energy selector.

The laser-driven particle beam irradiation apparatus may further include a beam intensity monitoring unit determining whether intensity of a laser-driven particle ray having the energy distribution converged by the energy distribution converging unit and having a particular energy width selected by the energy selector is normal or not, wherein, when the beam intensity monitoring unit determines that the intensity of the laser-driven particle ray is abnormal, the irradiation controller stops irradiation of the object with the laser-driven particle ray.

It may be desired that the beam intensity monitoring unit determines whether the intensity of the laser-driven particle ray per shot of pulsed laser light is normal or not, on the basis of a peak intensity of the energy distribution of the laser-driven particle ray.

In another aspect of the present invention, there is also provided a laser-driven particle beam irradiation method, comprising:

a particle beam generating step of irradiating a target with pulsed laser light to extract a laser-driven particle ray;

a beam converging step of spatially converging the laser-driven particle ray;

an energy selecting step of selecting an energy and an energy width of the laser-driven particle ray according to a depth of an irradiation position set in an object to be irradiated; and an irradiation step of adjusting the irradiation position of the laser-driven particle ray in the object to be irradiated, wherein, in the beam converging step, a magnetic field forcing divergence components of the laser-driven particle ray that go away from a center of the trajectory of the laser-driven particle ray back to the center of the trajectory is generated on the trajectory and the laser-driven particle ray is converged by the magnetic field.

This method may provide the following preferred embodiments or modes.

It may be desired that, in the beam converging step, degree of convergence of the laser-driven particle ray used in each step is adjusted by adjusting the magnetic field.

It may be desired that, in the energy selecting step, a magnetic field by which laser-driven particle rays are deflected according to momentums thereof is formed on the trajectory of the laser-driven particle rays and deflected laser-driven particle rays are screened on the basis of differences of trajectories to select an energy and an energy width of a laser-driven particle ray.

The laser-driven particle beam irradiation method may further comprise an energy distribution converging step of converging an energy distribution of the laser-driven particle ray to provide a peak at a particular energy.

The laser-driven particle beam irradiation method may further comprise a pulse width compressing step of reducing the pulse width of the laser-driven particle ray.

It may be desired that, in the pulse width compressing step, a high-frequency electric field induced by a pulse width compressing voltage is generated and the laser-driven particle ray is guided to and passed through the high-frequency electric field to reduce the pulse width of the laser-driven particle ray, the pulse width compressing voltage being defined as $$V > \frac{E_0 \beta_0^2 \gamma_0^2}{q} \cdot \frac{\sqrt{1 - m^2 c^4 / E_0^2}}{\sqrt{1 - m^2 c^4 / E_0^2} + fL/c}$$

wherein f is the frequency of the high-frequency voltage, L is the distance from a laser-driven particle ray emission point, $\beta_0$ and $\gamma_0$ are Lorentz factors, $E_0$ is the total energy of the laser-driven particle ray, c is the speed of light, m is the mass of the laser-driven-particle ray, and q is the charge of the laser-driven particle ray.

It may be desired that, after the energy distribution is converged in the energy distribution converging step and a particular energy and energy width are selected in the energy selecting step, determination is made as to whether intensity of the laser-driven particle ray is normal or not and, if it is determined that the intensity is abnormal, irradiation of the object with the laser-driven particle ray is stopped.

The determination may be performed as to whether the intensity of the laser-driven particle ray per shot of pulsed laser light is normal or not, on the basis of a peak intensity of the energy distribution of the laser-driven particle ray.

According to the present invention of the structures and characters mentioned above, the radiation therapy using laser-driven particle rays is enabled and the convergence of laser-driven particle rays can be increased while reducing deterioration of the intensity of the laser-driven particle rays in the course of transportation of the laser-driven particle rays to a diseased site of a patient.

The nature and further characteristic features of the present invention will be made clearer from the following description made with reference to the accompanying drawings.

BRIEF DESCRIPTION OF THE DRAWINGS

In the accompanying drawings:

FIG. 2 is diagram illustrating exemplary irradiation pattern data referred to by the laser-driven particle beam irradiation apparatus of FIG. 1;

FIG. 17 is a diagram illustrating an effect of high-frequency electric field control according to a third embodiment (result of a simulation), in which

DESCRIPTION OF THE PREFERRED EMBODIMENTS

Embodiments of a laser-driven particle beam irradiation apparatus and method according to the present invention will be described hereunder with reference to the accompanying drawings.

First Embodiment

Figure 1:
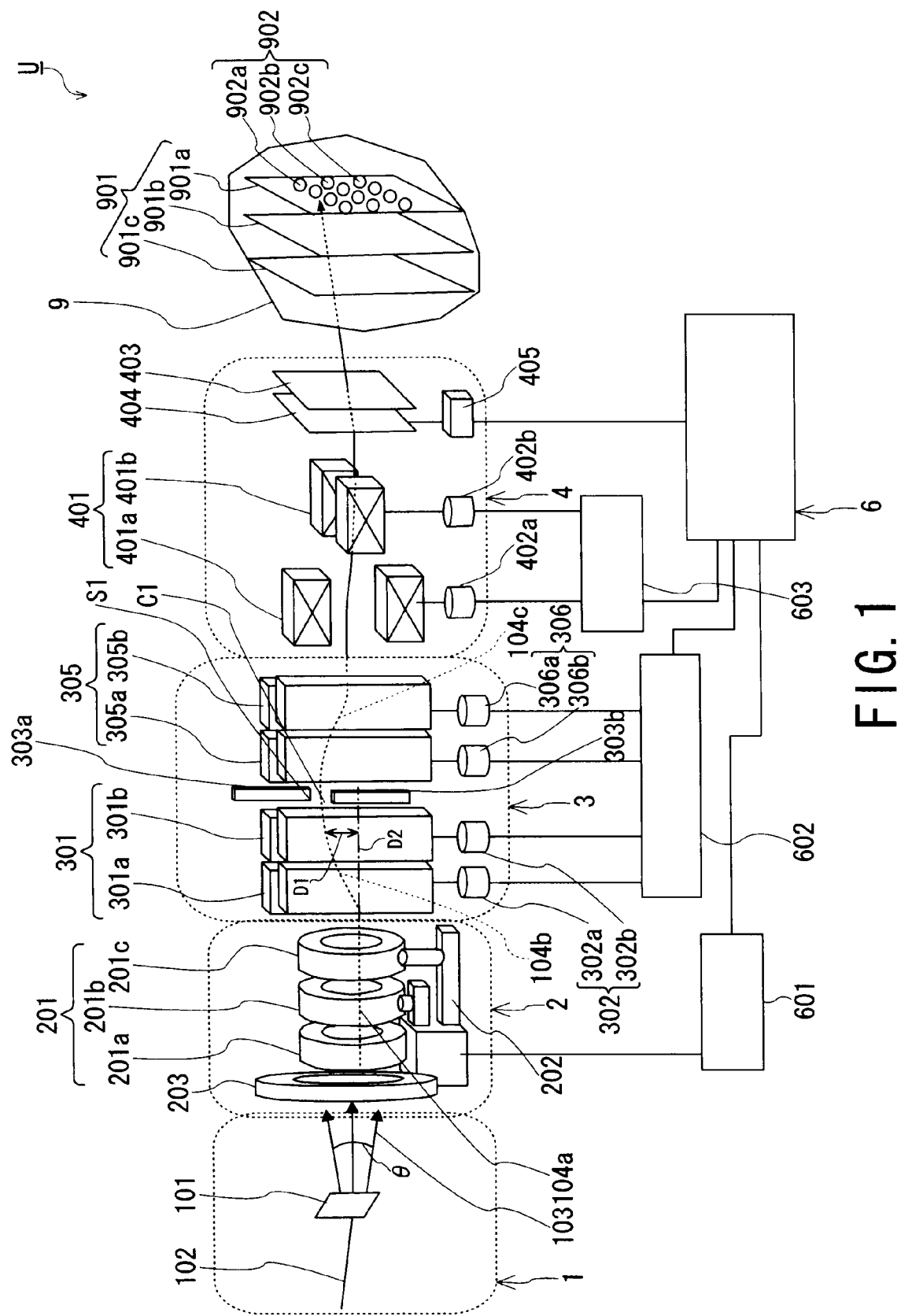
FIG. 1 is a diagram illustrating a first embodiment of a laser-driven particle beam irradiation apparatus according to the present invention.

With reference to FIG. 1 illustrating a first embodiment of a laser-driven particle beam irradiation apparatus U according to the present invention using laser-driven proton rays as its particle ray source for therapy radiation.

The laser-driven proton beam irradiation apparatus U includes a proton beam generator 1, a beam converging unit 2, an energy selector 3, an irradiation port 4, and an irradiation controller 6. Reference numeral 9 in FIG. 1 indicates a diseased site of a patient, for example.

(Proton Beam Generator)

The proton beam generator 1 irradiates a thin-film target 101 made of a metal or polymer with pulsed laser light 102 having a high intensity and an ultrashort wavelength to generate laser-driven proton rays 103. The proton beam generator 1 is configured so that a new target 101 is constantly provided on the irradiation trajectory of the pulsed laser light 102.

(Beam Converging Unit)

The beam converging unit 2 forms a transportation path which guides a laser-driven proton ray 103 to a diseased site 9 of a patient and converges the laser-driven proton ray 103, which is emitted from the proton beam generator 1 at a divergence angle θ. The beam converging unit 2 includes a quadrupole magnet 201, a QM actuator 202, and an angle collimator 203.

The quadrupole magnet 201 forms a magnetic field on the trajectory of a laser-driven proton ray 103 that forces divergence components of the laser-driven proton ray 103 that go away from the center of the trajectory back to the trajectory center. The magnetic field converges the laser-driven proton ray 103.

The quadrupole magnet 201 includes three quadrupole magnets 201a to 201c which are permanent magnets. The quadrupole magnets 201a to 201c are arranged along the transportation path of a laser-driven proton ray 103 so that the magnetic field converging the laser-driven proton ray 103 is multiply-exerted on the laser-driven proton ray 103. The number of quadrupole magnets may be varied appropriately in consideration of factors such as the control over the convergence of the laser-driven proton ray 103. Hereafter, a laser-driven proton ray converged with the quadrupole magnet 201 is referred to as "proton beam".

The QM actuator 202 moves at least one of the quadrupole magnets 201a to 201c along the transportation path of the laser-driven proton ray 103 under the control of the irradiation controller 6.

The angle collimator 203 blocks wide-angle components of a laser-driven proton ray 103 generated by the proton beam generator 1 from reaching the quadrupole magnet 201. The angle collimator 203 is provided between the target 101 in the proton beam generator 1 and the quadrupole magnet 201a closest to the target 101 and has a bore diameter smaller than that of an entrance for laser-driven proton rays 103 which is formed in the quadrupole magnet 201a. The angle collimator 203 is made of a low radioactivation material such as aluminum.

(Energy Selector)

The energy selector 3 is provided at the proton beam outlet of the beam converging unit 2 and adapted to select a proton beam having a particular energy and a particular energy width (or energy spread) from among proton beams 104a having continuous energy distributions converged by the beam converging unit 2. The energy selector 3 includes an energy separating magnet 301, an energy separating magnet power supply 302, an energy collimator 303, an EC actuator 304, an energy combining magnet 305, and an energy combining magnet power supply 306.

The energy separating magnet 301 generates a magnetic field that is variable in direction and magnitude under the application of an exciting current and uses this variable magnetic field so as to deflect the trajectory of a proton beam 104a converged by the beam converging unit 2 according to its momentum to thereby control the amount of deflection of the proton beam 104a. The energy separating magnet 301 includes two energy separating magnets 301a and 301b.

The energy separating magnet power supply 302, the output of which is controlled by the irradiation controller 6, applies a required exciting current to the energy separating magnet 301 to change the magnetic field generated by the energy separating magnet 301. The energy separating magnet power supply 302 includes energy separating magnet power supply sources 302a and 302b connected to the energy separating magnets 301a and 301b, respectively.

The energy collimator 303 includes two blocks 303a and 303b which are provided so as to block the transportation path of a proton beam 104b deflected and diffused by the energy separating magnet 301 according to a difference in momentum and are vertically movable, and a slit S1 which is defined by the blocks 303a and 303b and allows a proton beam 104b having a particular trajectory to selectively pass through the slit S1.

The EC actuator 304 moves the blocks 303a and 303b of the energy collimator 303 up and down under the control of the irradiation controller 6. For example, the EC actuator 304 enlarges or reduces the size of the slit S1 defined by the blocks 303a and 303b while retaining the slit center C1 of the slit S1 or moves the blocks 303a and 303b up and down so that the slit center C1 of the slit S1 is displaced while retaining the size of the slit S1.

The energy combining magnet 305 generates a magnetic field variable in direction and magnitude under the application of an exciting current. The variable magnetic field reconverges the trajectory of a proton beam 104b deflected and diffused through the energy separating magnet 301 according to its momentum. The energy combining magnet 305 includes two energy combining magnets 305a and 305b.

The energy combining magnet power supply 306, the output of which is controlled by the irradiation controller 6, applies a required exciting current to the energy combining magnet 305 so as to change the magnetic field generated by the energy separating magnet 301. The energy combining magnet power supply 306 includes energy combining magnet power supply sources 306a and 306b connected to the energy combining magnets 305a and 305b, respectively.

The numbers of energy separating magnets, energy separating magnet power supply sources, energy combining magnets, and energy combining magnet power supply sources may be changed appropriately in consideration of the controllability of deflection and combining of proton beams.

(Irradiation Port)

The irradiation port 4 is provided at the proton beam outlet of the energy selector 3 and controls the trajectory of a proton beam 104c with a particular energy that passed through the energy selector 3 so that the proton beam 104c is accurately applied to an irradiation spot 902 set at the diseased site 9 of a patient. The irradiation port 4 also serves to monitor the irradiation position and irradiation dose of the proton beam 104c at the diseased site 9.

The irradiation port 4 includes a scanning electromagnet 401, a scanning electromagnet power supply 402, a position monitoring unit 403, a dosimeter 404, and dosimeter circuit 405.

The scanning electromagnet 401, which is controlled by an exciting current, includes a horizontal scanning electromagnet 401a adjusting the trajectory of a proton beam 104c in the horizontal direction and a vertical scanning electromagnet 401b adjusting the trajectory of the proton beam 104c in the vertical direction. The scanning electromagnet power supply 402 (402a, 402b) supplies a current required for scanning of the proton beam 104c to the scanning electromagnet 401 (401a, 401b).

The position monitoring unit 403 outputs a signal indicative of the position of a proton beam 104c that passed the position monitoring unit 403, that is the position of incidence of the proton beam 104c at the diseased site 9 of the patient, and sends the signal to the irradiation controller 6. The position monitoring unit 403 may be an ionization-chamber position monitoring unit.

The dosimeter 404 outputs an electrical signal according to the intensity or dose of a proton beam 104c that passed the dosimeter 404, that is, the intensity or dose of the proton beam 104c applied to the diseased site 9 of the patient. The dosimeter 404 may be an ionization-chamber dosimeter.

The dosimeter circuit 405 receives an electrical signal output from the dosimeter 404 and, when the value of the received electrical signal reaches a preset integrated output value, sends a dose complete signal indicating that a preset dose has been applied to the irradiation spot 902 set at the diseased site 9 of the patient to the irradiation controller 6.

(Irradiation Controller)

The irradiation controller 6 is capable of recording irradiation pattern data specifying how therapy radiation for a patient should be performed. The irradiation controller 6 controls the entire laser-driven proton beam irradiation apparatus U with reference to the irradiation pattern data. The irradiation pattern data is generated from optimum irradiation information prepared in therapy planning before therapy radiation.

FIG. 2 illustrates exemplary irradiation pattern data referred to by the laser-driven proton beam irradiation apparatus U of FIG. 1.

The irradiation pattern data includes the relative horizontal and vertical positions 001 and 002 indicative of irradiation spots 902 (FIG. 1) viewed from a reference position, set for each of radiation slices 901 into which the diseased site 9 of the patient is virtually sliced, the range in patient 003 indicative of the position of a radiation slice 901, that is, the depth in patient, the beam stop position width in depth 004 indicative of the beam stop position width in depth in the patient, and the beam intensity 005 and set dose 006 to be applied to each irradiation spot 902. These items of information are required for controlling operation of the proton beam generator 1, the beam converging unit 2, the energy selector 3 and the irradiation port 4. The beam stop position width in depth is resulted from differences in the range in patient depending on the energy width of a proton beam. The irradiation pattern data can be changed as occasion demands.

The irradiation controller 6 includes a beam convergence controller 601, an energy selection controller 602 and a scan controller 603.

The beam convergence controller 601 adjusts the position of the quadrupole magnet 201 to adjust the focal position of laser-driven proton rays 103 at which the laser-driven proton rays 103 entering the quadrupole magnet 201 of the beam converging unit 2 converges. For example, the beam convergence controller 601 adjusts the relative positions of the quadrupole magnets 201a to 201c so that the focal point of the laser-driven proton ray 103 is formed on the diseased site 9 of the patient.

The position adjustment of the quadrupole magnets 201a to 201c is accomplished by driving the QM actuator 202 based on information indicating the positions of the quadrupole magnets 201a to 201c specified for the energy of each proton beam to be selected by the energy selector 3.

In order to select a proton beam having energy specified in the irradiation pattern data (see FIG. 2) among the proton beams that entered the energy selector 3, the energy selection controller 602 controls the output of the energy separating magnet power supply 302 to thereby adjust the exciting current applied to the energy separating magnet 301, thus adjusting the amount of deflections of the proton beams 104b.

The energy selection controller 602 also adjusts the position of the slit center C1 of the energy collimator 303 of the energy selector 3, as occasion demands, to select the trajectory of the proton beam 104c to pass the slit S1. The energy selection controller 602 controls the output of the energy combining magnet power supply 306 of the energy selector 3 to adjust the exciting current applied to the energy combining magnet 305 in order to converge the proton beam deflected and diffused by the energy separating magnet 301.

The energy selection controller 602 also adjusts the size of the slit S1 of the energy collimator 303 by operating the EC actuator 304 in order to adjust the beam stop position width in depth of the proton beam at the diseased site 9 of the patient. That is, the energy selection controller 602 displaces the blocks 303a and 303b up and down in mutually opposite directions so that a proton beam in an energy width capable of providing a required beam stop position width in depth at the diseased site 9 of the patient is selectively passed through the slit S1 of the energy collimator 303. The amount of displacement of the blocks 303a and 303b is set based on a beam stop position width in depth 004 contained in the irradiation pattern data (see FIG. 2).

The scan controller 603 controls the output of the scanning electromagnet power supply 402 so as to adjust the exciting current applied to the scanning electromagnet 401 so that the proton beam 104c enters with respect to a predetermined irradiation spot 902.

The laser-driven proton beam irradiation apparatus U of the structure mentioned above will operate in the following manner, which is based on an example in which therapy radiation is performed by using the so-called spot scanning radiation method. The spot scanning radiation method has been established in the field of the accelerator-driven particle beam irradiation technology and has been proven to be highly therapeutically effective.

In the spot scanning proton radiation method, the diseased site of a patient is virtually divided into three-dimensional grid points, that is, radiation slices and irradiation spots set in the radiation slices, and the diseased site is scanned with a proton beam in the direction of the depth of the diseased site (the direction along the proton beam axis D2) and in the direction of the cross-section of the diseased site (the direction intersecting the proton beam axis D2). When a dose complete signal indicating that a dose applied to one irradiation spot has reached a dose value set for the irradiation spot is generated, irradiation of the irradiation spot with the proton beam is stopped. Then, the proton beam is moved to the next irradiation spot or slice and irradiation is restarted. By repeating the operation, the entire diseased site is irradiated.

It is, for example, assumed that a therapy plan specifies that therapy radiation should be started at an irradiation spot 902a in the deepest radiation slice 901a, the radiation slice 901a is at a depth in patient of 156 mm, the energy of a proton beam that stops at the radiation slice 901a should be 150 MeV, and the beam stop position width in depth of the proton beam at the radiation slice 901a is 5 mm. In this case, the components of the laser-driven proton beam irradiation apparatus U are adjusted based on the treatment plan (irradiation pattern data) by the irradiation controller 6 as follows.

In the energy selector 3, the exciting current to be applied to the energy separating magnet 301, and as occasion demands, the position of the slit center C1 of the energy collimator 303 are adjusted to select a proton beam energy of 150 MeV.

At the same time, the size of the slit S1 of the energy collimator 303 in the energy selector 3 is adjusted to select an proton beam energy width of 1.8%, for example, as the energy width required for providing a beam stop position width in depth of 5 mm. An energy width of 1.8% (equivalent to a momentum width of 1%) can be selected by adjusting the size of the slit S1 of the energy collimator 303 to a value equal to 1% of the deflection distance D1 (the distance in the vertical direction viewed from the proton beam axis D2 not deflected) of the proton beam 104b. The exciting current to be applied to the energy combining magnet 305 is adjusted so that the proton beam, that has passed through the slit S1 of the energy collimator 303 and has been deflected and diffused, converges.

Figure 3:
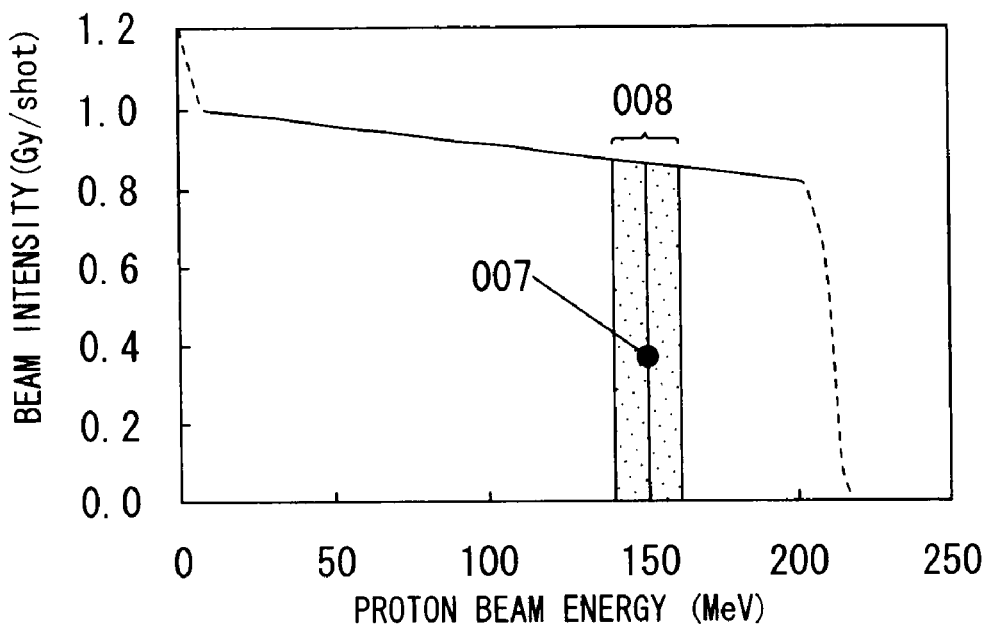
FIG. 3 is a diagram illustrating an example of a selected energy and energy width of a proton beam in the laser-driven particle beam irradiation apparatus of FIG. 1.
Figure 4:
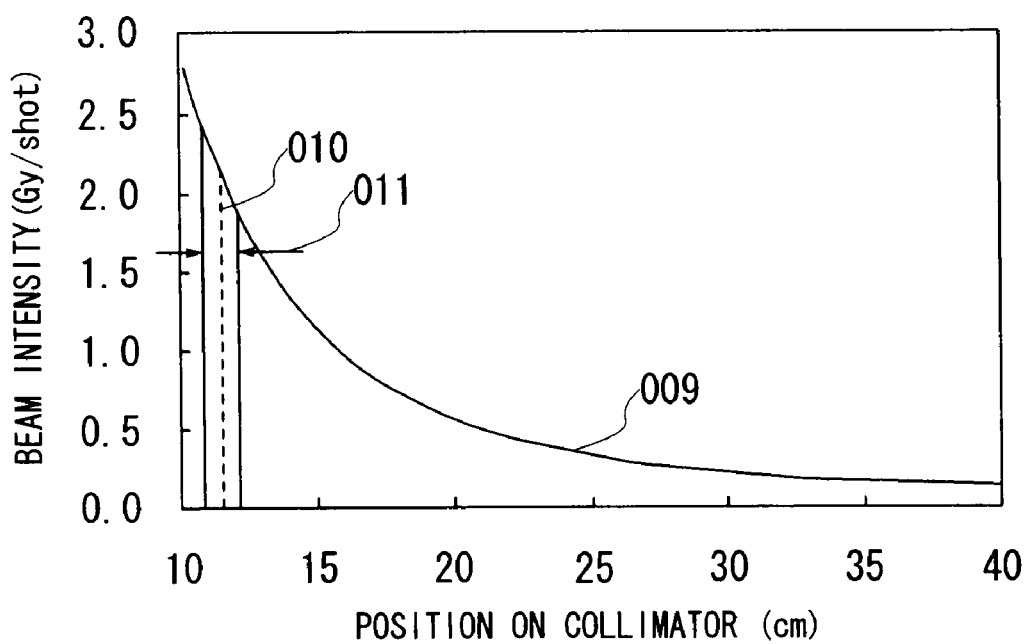
FIG. 4 is a diagram illustrating a state of an energy collimator when energy (150 MeV) and a beam stop position width in depth (5 mm) of a proton beam are selected in the laser-driven particle beam irradiation apparatus of FIG. 1.

FIG. 3 shows an example of a proton beam energy 007 (150 MeV) and energy width 008 (1.8%) of a proton beam selected in the laser-driven proton beam irradiation apparatus U. FIG. 4 schematically shows a state of the energy collimator 303 when a proton beam energy of 150 MeV and a beam stop position width in depth of 5 mm are selected in the laser-driven proton beam irradiation apparatus U, where reference numeral 009 indicates proton beam intensity, reference numeral 010 indicates the position of the slit center C1 (11 cm) of the energy collimator 303 with respect to the proton beam axis D2 (0 cm, see FIG. 1), and reference numeral 011 indicates the size of the slit S1 (1.1 mm) of the energy collimator 303.

The positions of the quadrupole magnets 201a to 201c in the beam converging unit 2 are adjusted according to the proton beam energy selected by the energy selector 3. As a result, the intensity of the proton beam with an energy of 150 MeV (energy width of 1.8%) required for the proton beam that reaches the diseased site 9 of a patient is provided.

The exciting current for the scanning electromagnet 401 in the irradiation port 4 is adjusted to adjust the trajectory of the proton beam so that the proton beam with an energy of 150 MeV (energy width of 1.8%) accurately enters the irradiation spot 902a.

After the components have been adjusted in this way, the proton beam generator 1 emits high-intensity, ultrashort-wavelength pulsed laser light 102 to a target 101 under the control of the irradiation controller 6 and the target 101 emits laser-driven proton rays 103 with a continuous energy at a divergence angle θ.

The laser-driven proton ray 103 emitted from the proton beam generator 1 is first guided to the beam converging unit 2. In the beam converging unit 2, the angle collimator 203 blocks wide-angle components of a proton beam 104 from entering the structure of the quadrupole magnet 201. On the other hand, laser-driven proton rays 103 that entered the magnetic field generated by the quadrupole magnet 201 gradually converges into a proton beam 104a as the proton rays 103 pass through the magnetic field.

The proton beam 104a is subjected to the converging operation by the beam converging unit 2 and is then guided to the energy selector 3. In the energy selector 3, the proton beam 104a enters the magnetic field generated by the energy separating magnet 301 and the trajectory of the proton beam 104a is deflected according to the momentum. The deflected proton beam 104b travels toward the slit S1 of the energy collimator 303, passes through the slit S1, and becomes a proton beam 104c having an energy of 150 MeV (with an energy width of 1.8%). Then, the proton beam 104c that has been deflected and diffused due to differences in momentum gradually converges as the proton beam 104c passes through the magnetic field generated by the energy combining magnet 305.

The proton beam 104c selected at the energy selector 3 is guided to the irradiation port 4. In the irradiation port 4, the proton beam 104c enters the magnetic field generated by the scanning electromagnet 401, where the trajectory of the proton beam 104c is adjusted in the horizontal and vertical directions. The proton beam 104c then travels toward an irradiation spot 902a set in a radiation slice 901a and therapy radiation is applied to the irradiation spot 902a.

During the irradiation, the irradiation controller 6 monitors, on the basis of a signal output from the position monitoring unit 403, whether the proton beam 104c, having the trajectory which has been adjusted, is correctly entering the irradiation spot 902a. If the irradiation controller 6 determines that the incident position is not correct, the irradiation controller 6 outputs an alert and stops the operation of the laser-driven proton beam irradiation apparatus U by using an interlock.

The irradiation of the irradiation spot 902a with the proton beam is continued until a dose complete signal is output from the dosimeter circuit 405. When the dose complete signal is output and input into the irradiation controller 6, irradiation proceeds to the next irradiation spot 902b. That is, the irradiation controller 6 refers to the irradiation pattern data to adjust the exciting current for the scanning electromagnet 401 so that the proton beam enters the next irradiation spot 902b, and the irradiation of the irradiation spot 902b with the proton beam is continued until the dose complete signal is again input into the irradiation controller 6.

The aforementioned operation will be repeated to accomplish irradiation of all irradiation spots 902 set to the radiation slice 901a.

After the completion of the irradiation in the radiation slice 901a, the irradiation proceeds to the next radiation slice 901b. That is, the irradiation controller 6 refers to the irradiation pattern data to adjust the energy selector 3 so that the proton beam is brought into rest at the position of the radiation slice 901b and also to adjust the irradiation port 4 so that the proton beam enters each of the irradiation spots, not shown, in the radiation slice 901b. The operation is repeated in sequence and the irradiation reaches the shallowest radiation slice 901c.

Here, in the assumption that the treatment plan specifies that the shallowest radiation slice 901c is at a depth in patient of 80 mm and the energy of the proton beam that is brought into rest at the position of the radiation slice 901c is 100 MeV, the energy width of a proton beam required for obtaining a beam stop position width in depth of 5 mm at the diseased site 9 of the patient differs from that for an energy of 150 MeV selected previously. This is because the range of the proton beam in patient, that is, the position at which the proton beam brought into rest, is not proportional to the energy.

Therefore, in order to obtain a beam stop position width in depth of approximately 5 mm as in the case where a proton beam energy of 150 MeV was selected, the size of the slit S1 of the energy collimator 303 is adjusted to a size different from the size set when a proton beam energy of 150 MeV was selected.

Figure 5:
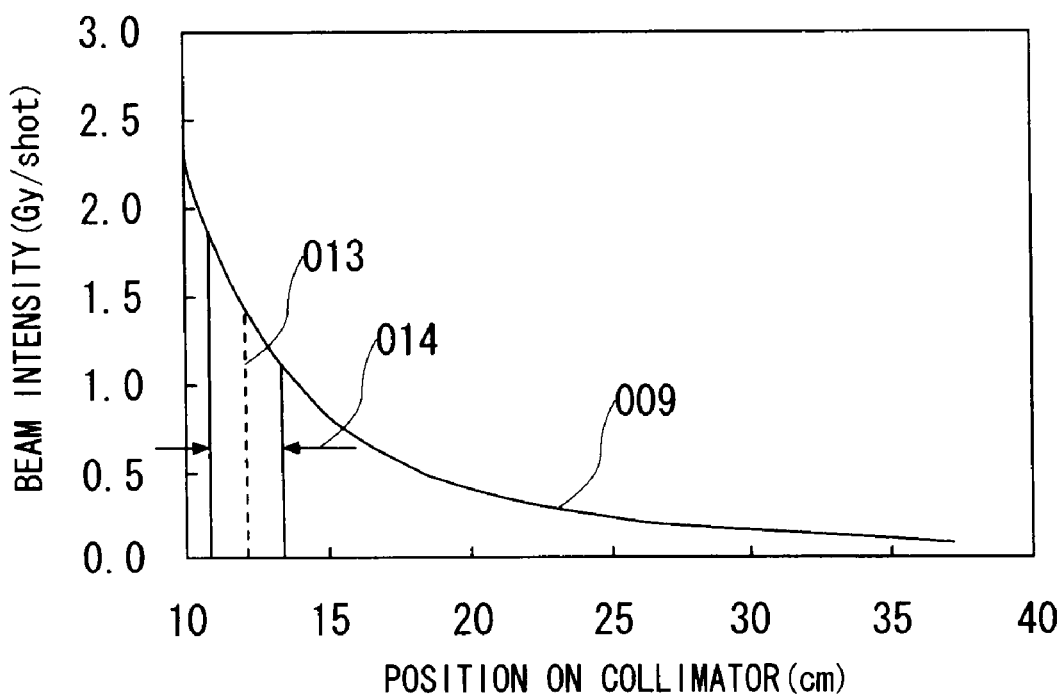
FIG. 5 is a diagram illustrating a state of an energy collimator when energy (100 MeV) and an energy width (5 mm) of a proton beam are selected in the laser-driven particle beam irradiation apparatus of FIG. 1.

Further, FIG. 5 shows a state of the energy collimator 303 when a proton beam energy of 100 MeV and a beam stop position width in depth of 5 mm are selected in the laser-driven proton beam irradiation apparatus U, where reference numeral 013 indicates the position (11 cm) of the slit center C1 with respect to the proton beam axis D2 (0 cm, see FIG. 1) and reference numeral 014 indicates the size of the slit S1 (2.6 mm).

FIG. 5 shows a state of the energy collimator 303 when the energy of the proton beam is selected by adjusting the amount of deflection of the proton beam 104b by controlling the exciting current applied to the energy separating magnet 301. Accordingly, the position of the slit center C1 of the energy collimator 303 (11 cm) is the same as in the case where a proton beam energy of 150 MeV was selected.

Figure 6:
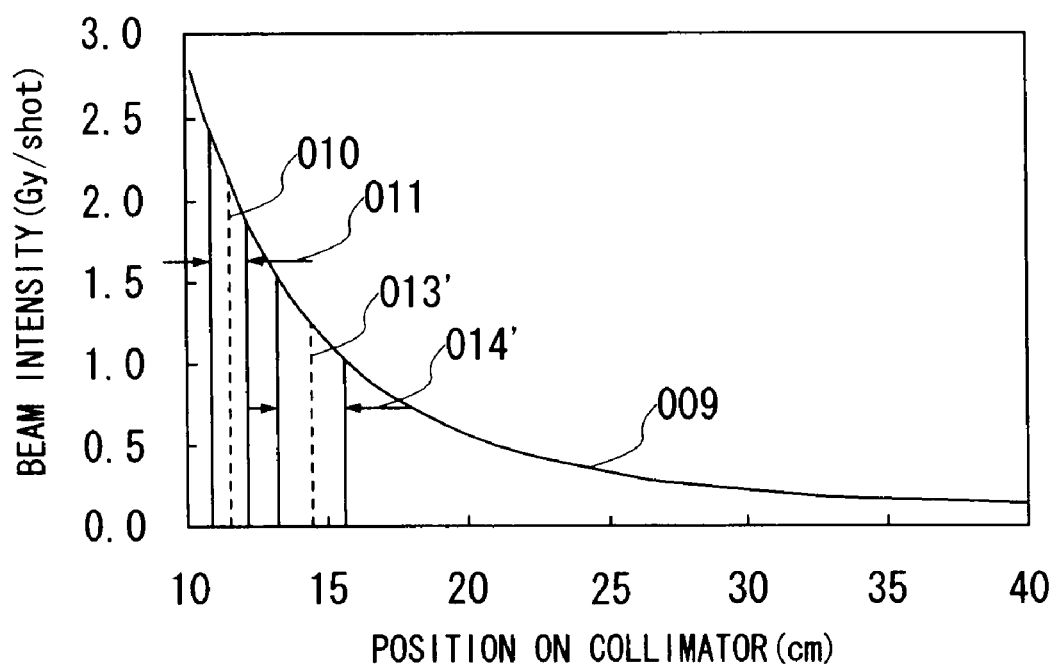
FIG. 6 is a diagram illustrating a variation of a method for selecting energy of a proton beam shown in FIG. 5.

However, the energy of the proton beam can also be selected by adjusting the position of the slit center C1 of the energy collimator 303 without or in conjunction with adjusting the amount of deflection of the proton beam 104b. FIG. 6 shows an exemplary variation of the method of selecting a proton beam energy, where reference numerals 013' and 014', like reference numerals 013 and 014, indicate the position of the slit center C1 with respect to the proton beam axis D2 and the size of the slit S1, respectively. As shown in FIG. 6, when a proton beam energy of 100 MeV is selected by this method, the slit center C1 is moved upward and the slit S is enlarged as compared with the case where an energy of 150 MeV was selected, so that a beam stop position width in depth of 5 mm is obtained.

Hereunder, the circumstance that had led to the present invention and effects of the laser-driven proton beam irradiation apparatus U will be described.

A laser-driven proton ray has the property of being emitted from a target at a divergence angle and spatially spreading. Therefore, when a laser-driven proton ray is used for radiation therapy, the exposed dose in normal tissue surrounding a diseased site must be reduced. That is, an operation is required for converging the laser-driven proton ray in the course of transportation of the laser-driven proton beam to a diseased site. However, when laser-driven proton rays are used, main components of a conventionally used accelerator-driven proton beam irradiation apparatus cannot be used for reasons described below.

In an accelerator-driven proton beam irradiation apparatus, a device, which is called range shifter, is used to adjust the range of an accelerator-driven proton beam in a patient. The range shifter includes acrylic plates with different thicknesses and allows a proton beam having a required energy to path through it to adjust the range of an accelerator-driven proton beam in the patient. For a laser-driven proton ray, the exposed dose in normal regions increases, whereas the intensity significantly decreases as the proton beam is transported to an irradiation spot, because the laser-driven proton ray is emitted from a target at a divergence angle. Scattering by the range shifter will result in further spatially spreading of the proton beam to further increase the exposed dose in normal regions.

In addition, a device, which is called ridge filter, is used in the accelerator-driven proton beam irradiation apparatus. The ridge filter acts to widen the beam stop position width in depth of an accelerator-driven proton beam having a very small energy width (a single energy) so that a steep dose distribution, called Bragg peak, matches the spacing between slices in the patient. However, a laser-driven proton ray has continuous energy, and therefore, it is meaningless to increase the beam stop position width in depth by the ridge filter. Instead, the scattering by the ridge filter would further spatially spread the proton beam, and therefore, would increase the drawback of increasing the radiation exposure in the normal regions.

In the proton beam radiation therapy, it is a necessary operation to select the proton beam energy and the energy width. When the laser-driven proton ray is used, the operation must be performed while reducing degradation of the intensity of the proton ray. However, the accelerator-driven proton beam irradiation apparatus does not have such an arrangement.

Therefore, the inventor has designed a laser-driven proton beam irradiation apparatus capable of adjusting the energy and energy width of a laser-driven proton ray while minimizing spatial spread and degradation of the intensity of the laser-driven proton ray, thereby realizing the therapy radiation using laser-driven particle rays.

Figure 7:
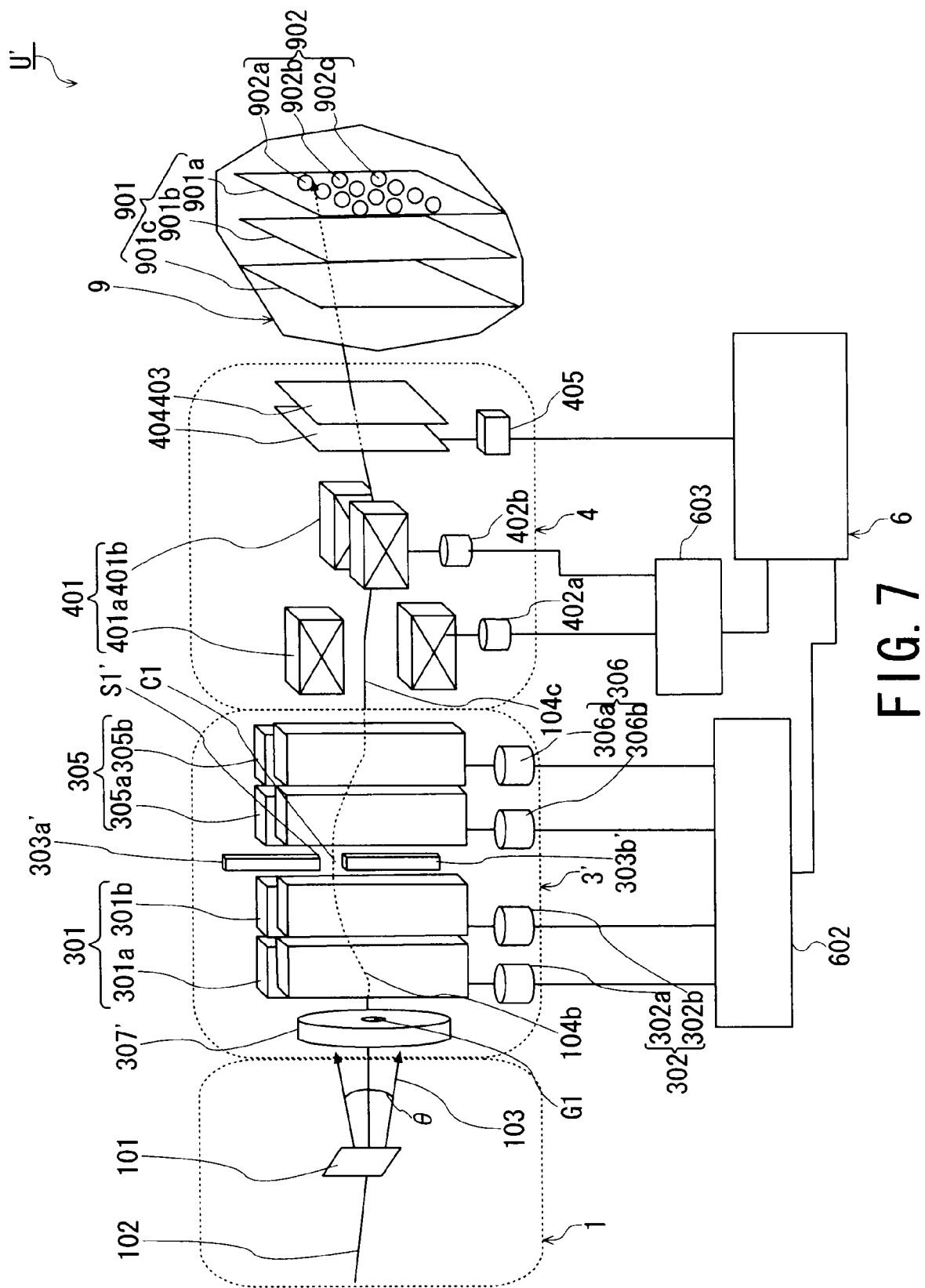
FIG. 7 is a diagram illustrating another embodiment of a laser-driven particle beam irradiation apparatus according to the present invention.

FIG. 7 shows an alternative embodiment of a laser-driven proton beam irradiation apparatus according to the present invention, which is an example for comparison with the laser-driven proton beam irradiation apparatus U according to the first embodiment. The same components as those of the first embodiment are labeled with the same reference numerals, and duplicated description thereof will be omitted.

The laser-driven proton beam irradiation apparatus U' according to the alternative embodiment of FIG. 7 includes an energy selector 3'. The energy selector 3' includes a converging collimator 307' and an energy collimator 303'.

The converging collimator 307' of the energy selector 3' is positioned so as to block the path of a laser-driven proton ray 103 generated by a proton beam generator 1 and has an opening G1' to allow a part of the laser-driven proton ray 103 to pass through it. The converging collimator 307' is made of a low radioactivation material such as aluminum.

The energy collimator 303' of the energy selector 3' includes two blocks 303a' and 303b' provided so as to block the path of a proton beam 104b deflected by the energy separating magnet 301 according to a difference in momentum and a slit S1' defined by the blocks 303a' and 303b'.

In the laser-driven proton beam irradiation apparatus U', the converging collimator 307' is provided on the upstream side from the energy separating magnet 301, so that the wide-angle components of the laser-driven proton ray 103 are removed from the beam path before the laser-driven proton ray 103 enters the energy selector 3'. As a result, precise irradiation restricted to an irradiation spot 902 specified in a treatment plan can be achieved and the exposed dose in normal tissue can be reduced.

In the energy selector 3' of the laser-driven proton beam irradiation apparatus U', the proton beam 104a enters the magnetic field generated by the energy separating magnet 301, and consequently, the trajectory of the proton beam 104a is deflected according to the momentum. The deflected proton beam 104b passes through the slit S1' and has a particular energy. The proton beam 104c enters the magnetic field generated by an energy combining magnet 305, where the proton beam 104b deflected and diffused due to difference in momentum is re-converged.

In this way, the laser-driven proton beam irradiation apparatus U' is capable of setting the range of a proton beam in a patient and the beam stop position width in depth without using a range shifter and ridge filter used in accelerator-driven particle beam apparatus. Accordingly, the laser-driven proton rays 103 are not scattered by the range shifter and ridge filter, and therefore, the spatial spread of the beam at a diseased site can be prevented. Thus, the radiation exposure in the normal regions surrounding the diseased site can be prevented.

However, for the laser-driven proton beam irradiation apparatus U', in order to increase the convergence of a proton beam, it is necessary to reduce the size of the opening G1' of the converging collimator 307', which will decrease the intensity of the proton beam that passes through the converging collimator 307' and eventually reaches the diseased site 9 of the patient.

For example, it is now assumed that the divergence angle θ of a laser-driven proton ray 103 is 5 degrees and the glancing angle in the slit S1 passing region of the energy selector 3' viewed from the emission point of the laser-driven proton ray 103 at a target 101 is set to 0.5 degrees in order to set an appropriate beam size and beam stop position width in depth at the diseased site 9. In this case, the intensity of the proton beam 104a guided to the energy selector 3' is less than or equal to approximately 1% of the intensity of the laser-driven proton ray 103 immediately after being emitted from the target 101.

The energy width of the proton beam used in the typical therapy radiation is approximately 2 to 5%. Therefore, the intensity of the proton beam 104c that passed through the energy selector 3' is further degraded. Depending on the intensity of pulsed laser light 102 to be applied and other conditions, experience has shown that the irradiation of a diseased site 9 of 10 cc, for example, with a dose of 2 Gy using the laser-driven proton beam irradiation apparatus U' requires approximately 100 minutes. It is however undesirable to hold the patient in place for such a long time, and there has been a demand for minimizing degradation of the intensity by increasing the convergence. This is a first issue concerning the laser-driven proton beam irradiation apparatus U'.

In addition, when the energy of a proton beam is changed from 150 MeV to 100 MeV according to the depth of a diseased site 9 in the patient in the laser-driven proton beam irradiation apparatus U', a beam stop position width in depth of 5 mm set for an energy of 150 MeV cannot be obtained for an energy of 100 MeV as described above, but a beam stop position width in depth of only approximately 2 mm, for example, will result.

As a method for obtaining a uniform dose distribution, it may be considered to set the distance between radiation slices to a value equal to the smallest beam stop position width in depth. This method can provide a highly uniform dose distribution. However, the reducing of the distance between radiation slices increases the number of radiation slices required for irradiation of the entire diseased site 9, which increases the irradiation time (including the time required for controlling the energy selector 3'), which increases the burden on the patient.

Then, as a method for obtaining a uniform dose distribution without increasing the irradiation time, the consideration may be made, during treatment planning, on the beam stop position width in depths that vary according to proton beam energies to be selected and on the setting of a distance between radiation slices that provides a uniform dose distribution. However, irradiation pattern data such as data on radiation slices and irradiation spots can usually be set based on image data taken using CT (Computed Tomography) (usually images are taken at evenly spaced positions). If radiation slices are to be prepared separately, additional time for calculations for optimizing the irradiation and additional costs for developing the optimization calculations and a laser-driven proton beam irradiation apparatus would be required.

That is, it has been required for the laser-driven proton beam irradiation apparatus U' to achieve a high uniformity of the dose distribution without reducing the distance between radiation slices or performing irradiation optimizing calculation. This is a second issue concerning the laser-driven proton beam irradiation apparatus U'.

In view of the above circumstance, the inventor has improved the laser-driven proton beam irradiation apparatus U' and adopted the configuration of the laser-driven proton beam irradiation apparatus U of the first embodiment.

Figure 8:
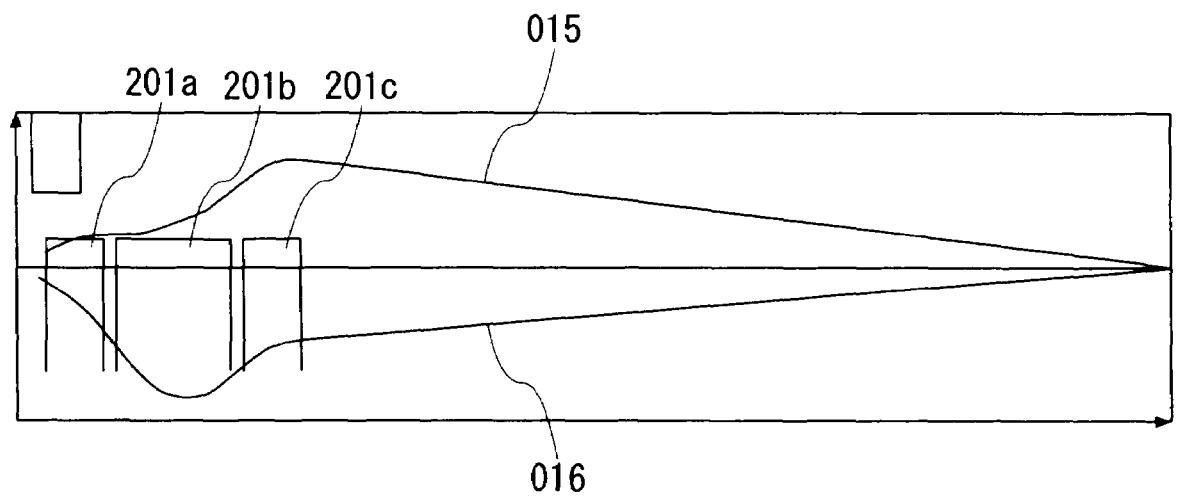
FIG. 8 is a diagram illustrating the result of a simulation of a proton beam trajectory in the laser-driven proton beam irradiation apparatus of FIG. 1.
Figure 9:
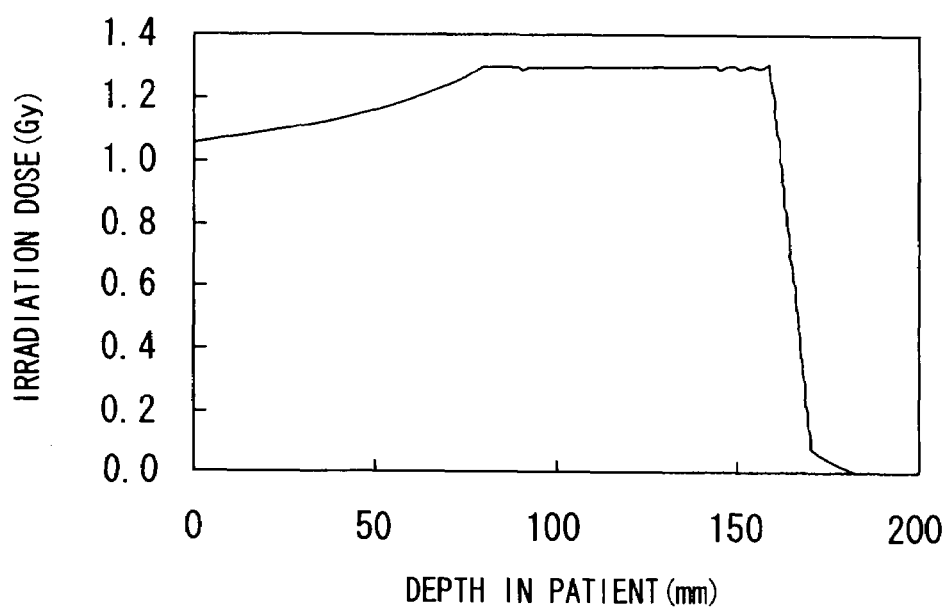
FIG. 9 is a diagram illustrating superposition of dose distributions on a radiation slice formed by the laser-driven particle beam irradiation apparatus of FIG. 1.
Figure 10:
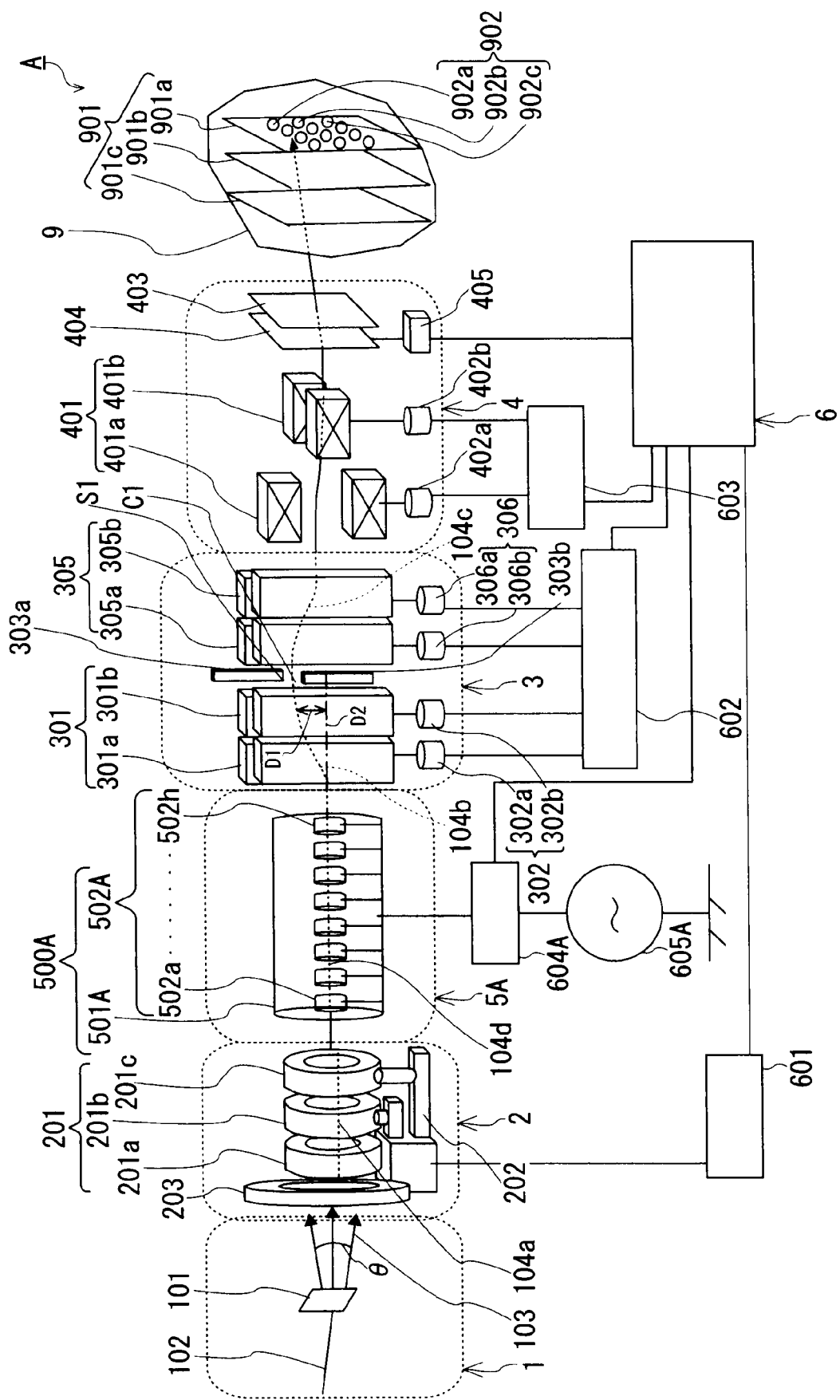
FIG. 10 is a diagram illustrating a second embodiment of a laser-driven proton beam irradiation apparatus according to the present invention.

FIGS. 8 to 10 are diagrams illustrating functions of the laser-driven proton beam irradiation apparatus U.

Hereunder, compatibility of convergence and intensity of proton beam will be discussed.

In the laser-driven proton beam irradiation apparatus U according to the present embodiment, a laser-driven proton ray 103 generated by the proton beam generator 1 is passed through the magnetic field generated by the quadrupole magnet 201 provided in the beam converging unit 2 to thereby converge the laser-driven proton ray 103.

FIG. 8 shows the result of a simulation of the trajectory of a proton beam 104a of the laser-driven proton beam irradiation apparatus U. The horizontal axis represents the distance in the direction of travel of the proton beam and the vertical axis represents the distance in the direction of the spread of the proton beam. Reference numerals 201a to 201c in FIG. 8 indicate the positions of the quadrupole magnets 201a to 201c in the beam converging unit 2. Reference numeral 015 represents the trajectory of the proton beam in the horizontal direction and reference numeral 016 represents the trajectory of the proton beam in the vertical direction.

As shown in FIG. 8, in the laser-driven proton beam irradiation apparatus U, the convergence of the laser-driven proton ray 103 can be well increased while degradation of the intensity being minimized without using a converging collimator 307' provided in the laser-driven proton beam irradiation apparatus U'.

It has been found that approximately 36% in intensity of the laser-driven proton ray 103 is guided to the energy selector 3, in a case where the divergence angle θ of the laser-driven proton ray 103 is 5 degrees and the glancing angle in the slit S1 passing region of the energy selector 3 viewed from the laser-driven proton rays 103 emission point in the target 101 is 0.5 degrees.

On the other hand, in the laser-driven proton beam irradiation apparatus U', only approximately 1% or less of the laser-driven proton rays 103 is guided to the energy selector 3', as described above. Therefore, by using the quadrupole magnet 201 as means for converging the laser-driven proton rays 103, a proton beam having an intensity approximately 40 times higher than that in the apparatus using the converging collimator 307' can be provided.

Since the degradation of the intensity of the laser-driven proton beam can be significantly reduced while increasing the convergence of the laser-driven proton beam, the time required for therapy radiation, which was for example 100 minutes in the laser-driven proton beam irradiation unit U', can be reduced to a few minutes.

Hereunder, compatibility between the selection of the proton beam energy and the energy width and the intensity of the proton beam will be explained.

A proton beam 104a converged by passing through the beam converging unit 2 of the laser-driven proton beam irradiation apparatus U is guided to the energy selector 3. In the energy selector 3, the proton beam 104a enters the magnetic field generated by the energy separating magnet 301, and the trajectory of the proton beam 104a is deflected according to the momentum. The deflected proton beam 104b passes through the slit S1 and becomes a proton beam 104c having a particular energy. The proton beam 104c then passes through the magnetic field generated by the energy combining magnet 305, and the proton beam 104b deflected and diffused due to difference in momentum is unified.

In this way, like the laser-driven proton beam irradiation apparatus U', the laser-driven proton beam irradiation apparatus U is capable of setting the range in a patient of a proton beam and a beam stop position width in depth without using a range shifter and a ridge filter used in accelerator-driven particle beam irradiation apparatus.

The dose distribution uniformity will be now mentioned hereunder.

In the laser-driven proton beam irradiation apparatus U, the energy width of a proton beam passing through the energy collimator 303 is adjusted each time a radiation slice 901 is changed, so that a constant beam stop position width in depth is provided.

That is, when the exciting current applied to the energy separating magnet 301 is adjusted to select a proton beam energy in the energy selector 3, the irradiation controller 6 refers to irradiation pattern data to increase or decrease the size of the slit S1 of the energy collimator 303 so that a beam stop position width in depth specified in the treatment plan is provided.

Therefore, a highly uniform dose distribution can be provided even if evenly spaced radiation slices set by using image data taken by CT are set. That is, the highly uniform dose distribution can be provided without reducing the spacing between radiation slices or performing irradiation optimization calculations. FIG. 9 shows superposition of dose distributions (the results of a simulation) on the radiation slices formed by the laser-driven proton ray irradiation apparatus U, where the horizontal axis represents the depth (mm) in the patient and the vertical axis represents irradiation dose (Gy).

Further, as can be seen from FIG. 9, the laser-driven proton beam irradiation apparatus U provides a highly uniform dose distribution at a depth in the range from 156 to 80 mm.

As to safety, the following will be mentioned.

Wide-angle components of a laser-driven proton ray 103 emitted from the proton beam generator 1 at a divergence angle θ are blocked before they enter the beam converging unit 2. This prevents proton rays from reaching the quadrupole magnet 201 provided in the trajectories of divergence of the laser-driven proton ray 103, thereby preventing radioactivation of the material of the quadrupole magnet 201 from causing. Further, in the proton beam 104 that eventually will reach the diseased site 9 of the patient, components that stray outside the irradiation spot 902 specified in the preliminary treatment plan are eliminated, and therefore, the exposed dose in normal tissue is reduced.

Advantageous effects of the laser-driven proton beam irradiation apparatus U will be described hereunder.

(1) The laser-driven proton beam irradiation apparatus U includes: a particle beam generator irradiating a target 101 with pulsed laser light 102 to thereby emit a laser-driven proton ray 103; a beam converging unit 2 forming a transportation path which guides the emitted laser-driven proton ray 103 to a diseased site 9 of a patient and spatially converging the laser-driven proton ray 103; an energy selector 3 selecting an energy and an energy width of the laser-driven proton ray 103; an irradiation port 4 causing the laser-driven proton ray 103 to scan the diseased site 9 so as to adjust an irradiation position in the diseased site 9; and an irradiation controller 6 controlling the operations of the particle beam generator 1, the beam converging unit 2, the energy selector 3, and the irradiation port 4, respectively. This configuration enables therapy radiation using laser-driven proton rays. That is, the need of an accelerator is eliminated, and the proton therapy radiation that advantageously uses a compact and space-saving apparatus can be accomplished.

Furthermore, the beam converging unit 2 generates a magnetic field on the trajectory of the laser-driven proton ray 103 that forces divergence components of the laser-driven proton ray 103 that go away from the center of the trajectory back to the center of the trajectory. The magnetic field converges the laser-driven proton ray 103. Therefore, the convergence of the laser-driven particle ray can be increased while reducing degradation of the intensity of the laser-driven proton ray 103 during transportation of the laser-driven particle ray to the diseased site of the patient.

(2) The beam converging unit 2 is provided between the proton beam generator 1 and the energy selector 3. Therefore, a laser-driven proton ray 103 emitted from the target 101 at a divergence angle θ is spatially converged and then subjected to the selection of energy and energy width. As a result, the laser-driven proton ray 103 having a high intensity can be obtained as compared with that in a configuration in which the beam converging unit 2 is located after the energy selector 3. Thus, the advantageous effect described in (1) is enhanced.

(3) The beam converging unit 2 includes the quadrupole magnet 201 consisting of permanent magnets. The quadrupole magnet 201 generates a magnetic field converging a laser-driven proton ray 103. Therefore, a compact, low-cost laser-driven proton beam irradiation apparatus U can be realized as compared with an apparatus in which an electromagnet is used to adjust a magnetic field through exciting current adjustment to converge laser-driven proton rays 103.

(4) The quadrupole magnet 201 of the beam converging unit 2 includes multiple quadrupole magnets provided along the transportation path of laser-driven proton rays 103 and at least one of the magnets 201 is movable. Therefore, the spatial distribution of the laser-driven proton ray 103 can be adjusted. As a result, the convergence and intensity of the laser-driven proton ray 103 that reaches the diseased site 9 of the patient can be retained high, thereby further increasing the advantageous effect described in the above (1).

(5) The beam converging unit 2 includes the angle collimator 203 provided between the quadrupole magnet 201 and the target 101 of the proton beam generator 1 and blocks wide-angle components of a laser-driven proton ray 103 from reaching the quadrupole magnet 201. Accordingly, the exposed dose in normal tissue outside the diseased site 9 can be minimized and the safety of therapy radiation is improved.

(6) The energy selector 3 generates a magnetic field in the transportation path of laser-driven proton rays 103 that deflects laser-driven proton rays 103 according to their momentums. The energy selector 3 also selects a laser-driven proton ray 103 that has a particular trajectory and eliminate the other laser-driven proton rays 103 from the transportation path, thereby selecting the laser-driven proton ray 103 energy and energy width.

Accordingly, dispersion of laser-driven proton rays 103 does not affect the operation of selecting the laser-driven proton ray 103 energy and energy width. As a result, the laser-driven proton ray 103 can be transported to the diseased site 9 with a high intensity. Thus, the advantageous effect described in the above (1) is further increased.

(7) The energy selector 3 includes the energy separating magnet 301 including an electromagnet that forms a variable magnetic field under the control of an exciting current and the energy collimator 303. The energy collimator 303 is provided so as to block the transportation path of laser-driven proton rays 103 deflected by the variable magnetic field and is provided with the slit S1 that selectively allows a laser-driven proton ray 103 having a particular trajectory to pass through the slit S1. Therefore, the advantageous effect described in the above (6) can be reliably and readily achieved.

(8) The energy collimator 303 of the energy selector 3 is formed in such a manner that the size of the slit S1 can be adjusted. Therefore, a highly uniform dose distribution can be achieved and the precision of therapy radiation can be improved without reducing the space between radiation slices or without performing irradiation optimization calculations.

Second Embodiment

FIG. 10 illustrates a second embodiment of a laser-driven proton beam irradiation apparatus according to the present invention, and this second embodiment includes, in addition to the components of the laser-driven proton beam irradiation apparatus U of the first embodiment, arrangements relating to a proton beam energy selecting function and an interlock of the laser-driven proton beam irradiation apparatus U.

Hereunder, the same components as those of the first embodiment are labeled with the same reference numerals or symbols for omitting the duplicated description thereof, and as to components that are variations of those of the first embodiment and newly added components, reference numerals are additionally appended with "A".

The laser-driven proton beam irradiation apparatus A according to the second embodiment includes an energy distribution converging unit 5A and a beam intensity monitoring unit 7A as shown in FIG. 10. An irradiation controller 6A of the laser-driven proton beam irradiation apparatus A includes an energy distribution convergence controller 604A and a high-frequency power supply 605A.

(Energy Distribution Converging Unit)

The energy distribution converging unit 5A is provided between a proton beam generator 1 and an energy selector 3 as shown in FIG. 10. The energy distribution converging unit 5A forms the transportation path of a laser-driven proton ray 103. The energy distribution of the laser-driven proton ray 103 is converged in the transportation path to provide a peak at a particular energy. The energy distribution converging unit 5A is formed with a phase rotation cavity unit 500A including an outer cavity 501A and inner cavities 502A.

Figure 11:
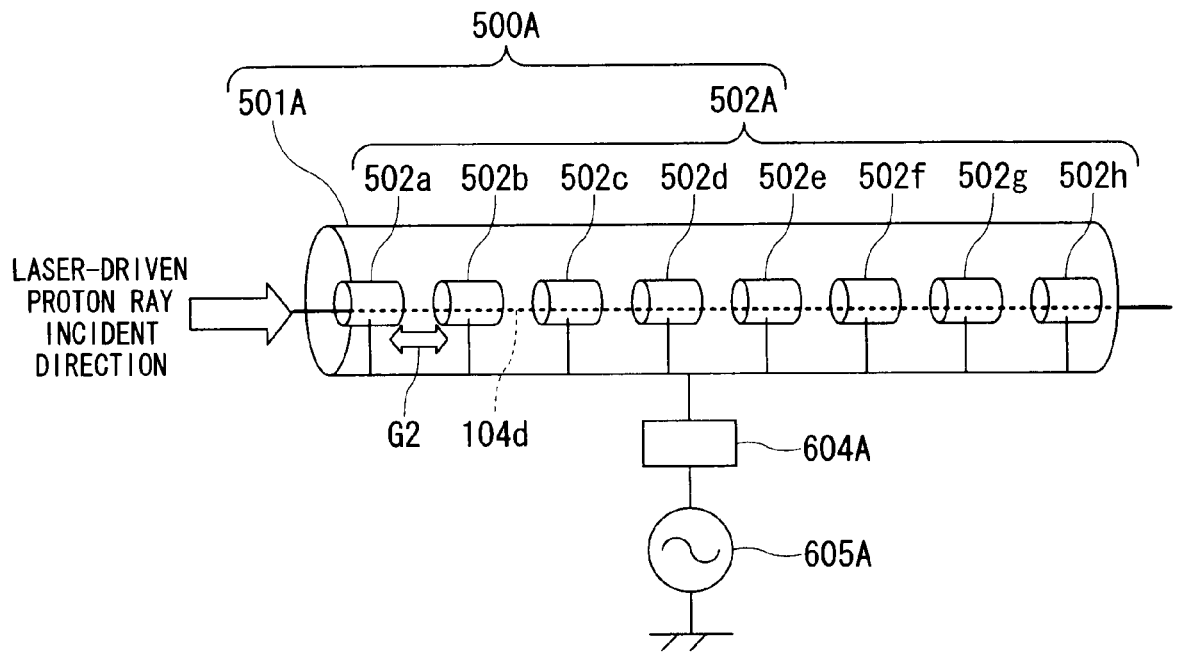
FIG. 11 is an enlarged view of a phase rotation cavity unit of the laser-driven proton beam irradiation apparatus of FIG. 2.

FIG. 11 is an enlarged view of the phase rotation cavity unit 500A of the laser-driven proton beam irradiation apparatus A.

The outer cavity 501A of the phase rotation cavity unit 500A constitutes an outer configuration of the transportation path of a proton beam 104d that passed a beam converging unit 2.

The inner cavities 502A of the phase rotation cavity unit 500A are formed inside the outer cavity 501A and spaced along the longitudinal direction thereof the outer cavity 501A. A high-frequency voltage is applied to the inner cavities 502A from the high-frequency power supply 605A.

The inner cavities 502A applies a high-frequency electric field to the proton beam 104d passing through gaps G2 between adjacent inner cavities 502A to converge the energy distribution of the proton beam 104d around the energy of protons that enter each gap G2 in synchronization with the phase of the high-frequency voltage applied to the inner cavities 502A among the protons that make up a proton bunch (time-discrete state of protons).

Figure 12:
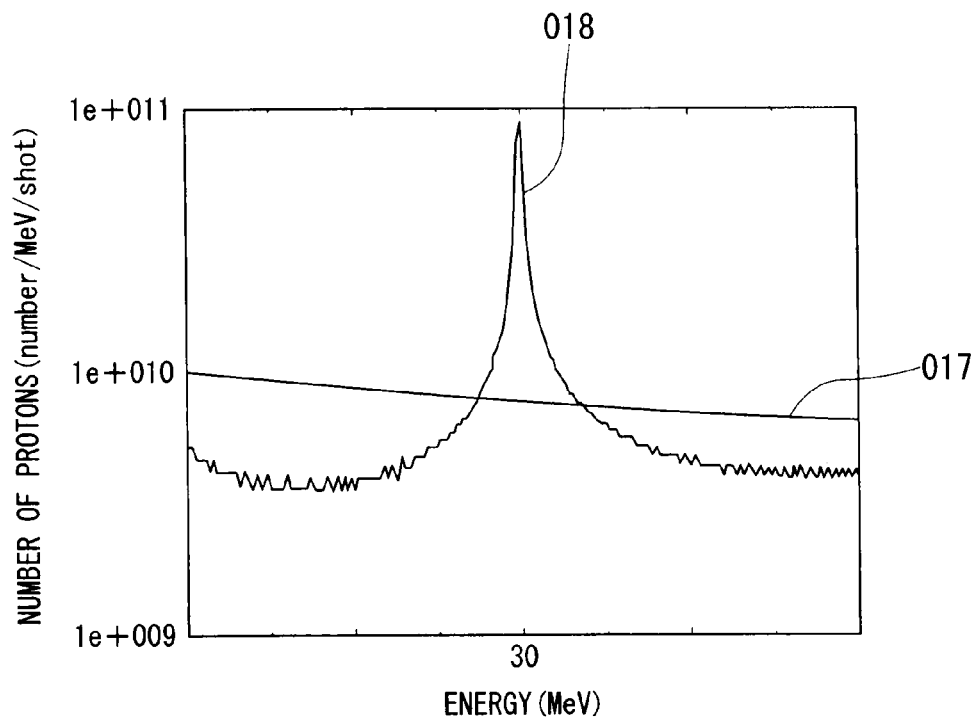
FIG. 12 is a diagram illustrating an energy distribution of a proton beam that passed through the phase rotation cavity unit of FIG. 2 (the result of a simulation)

FIG. 12 shows a graph of the energy distribution of a proton beam that passed through the phase rotation cavity unit 500A of the laser-driven proton beam irradiation apparatus A (results of a simulation), in which the horizontal axis represents energy of proton and the vertical axis represents the number of protons per shot of pulsed laser light 102. In FIG. 12, reference numeral 017 represents the energy distribution of a proton beam in the absence of a high-frequency electric field applied to the phase rotation cavity unit 500A and reference numeral 018 represents the energy distribution of the proton beam in the presence of the high-frequency electric field applied to the phase rotation cavity unit 500A.

The energy distribution converging unit 5A is preferably provided between the beam converging unit 2 and the energy selector 3. This is because the intensity of the proton beam reaching the diseased site 9 of a patient can be retained to be high if the energy distribution of the proton beam is converged at the energy distribution converging unit 5A and the energy of the proton beam is selected at the energy selector 3 in comparison with a case reverse thereto. That is, the beam converging unit 2, the energy distribution converging unit 5A, the energy selector 3, and the irradiation port 4 are preferably arranged in this order from the upstream side of the proton beam transportation path as shown in FIG. 10 in term of the retaining of the intensity of the proton beam.

[Irradiation Controller]

The energy distribution convergence controller 604A of the irradiation controller 6A adjusts the position of the energy peak of a proton beam 104d passing through the phase rotation cavity unit 500A. The energy peak position adjustment is performed by controlling the phase of the high-frequency voltage to be applied to the inner cavities 502A of the energy distribution converging unit 5A based on the range in patient 003 (FIG. 2) specified for each radiation slice position contained in the irradiation pattern data.

The phase of the high-frequency voltage is controlled by applying a high-frequency voltage that satisfies the following Equation (1) to the high-frequency power supply 605A.

[Equation 1]

$$\frac{2fL}{v_0} + \frac{\phi}{\pi} = 2n + 1 (A) \quad (1)$$

Herein, f is the frequency of the high-frequency electric field, $\phi$ is the phase of the high-frequency electric field, L is the distance from the proton emission point of a target, $E_0$ (mentioned below) is the desired energy peak of the proton beam, $v_0$ is the proton velocity corresponding to $E_0$, and n is an integer.

That is, the energy distribution convergence controller 604A adjusts the phase $\phi$ of the high-frequency voltage to be applied to the inner cavities 502A and provides the energy peak around the desired energy $E_0$ in the energy distribution of the proton beam 104d passing through the phase rotation cavity unit 500A according to Equation (1). The amplitude of the high-frequency voltage preferably satisfies k=1/L ($k=2\pi qVf/c^2\beta_0^3\gamma_0^2 E_0$) in order to converge the energy distribution, wherein q is the charge of the proton, $\beta_0$ and $\gamma_0$ are Lorentz factors, and c is the speed of light.

Figure 13:
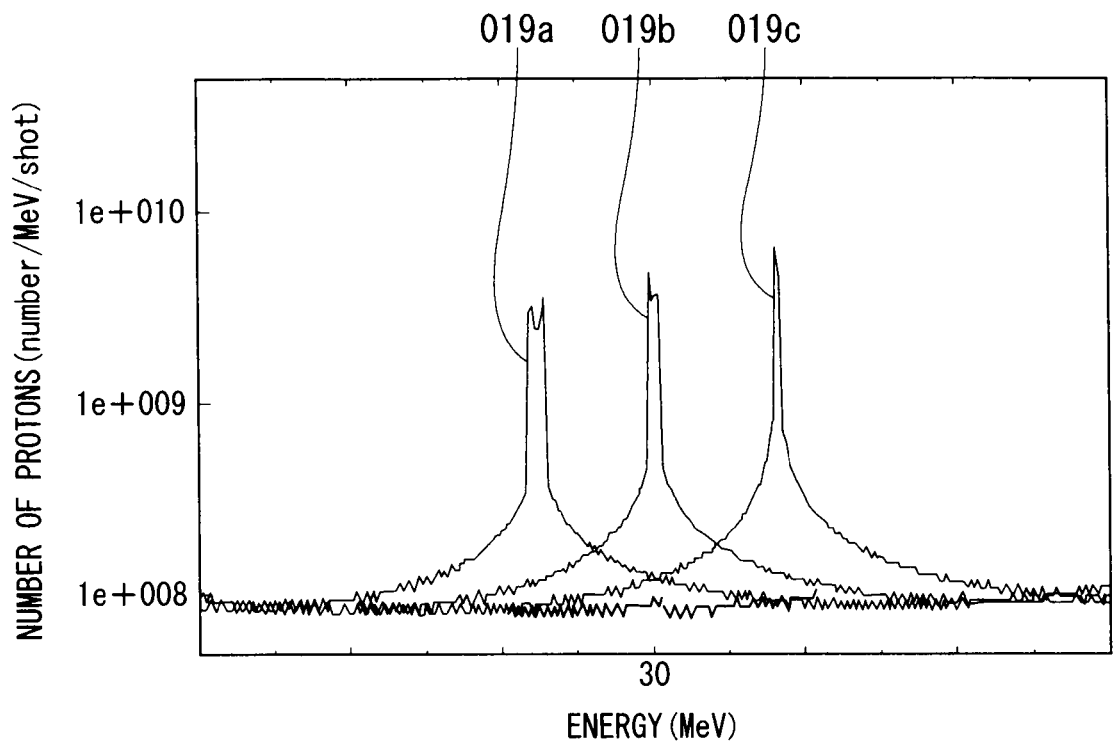
FIG. 13 illustrates an example of changes of the energy peak of a proton beam in the laser-driven particle beam irradiation apparatus of FIG. 2 (the result of a simulation)

FIG. 13 shows a graph of changes of the energy peak of a proton beam in the laser-driven proton beam irradiation apparatus A (results of a simulation), where the horizontal and vertical axes are the same as those in FIG. 12. In FIG. 13, reference numerals 019a to 019c represent different energy peaks resulting from position adjustments through phase rotation control.

If the irradiation controller 6A receives an abnormal signal from the beam intensity monitoring unit 7A, the irradiation controller 6A stops operation of the laser-driven proton beam irradiation apparatus A by means of an interlock.

(Beam Intensity Monitoring Unit)

The beam intensity monitoring unit 7A constantly monitors the intensity of a proton beam 104c per shot.

Figure 14:
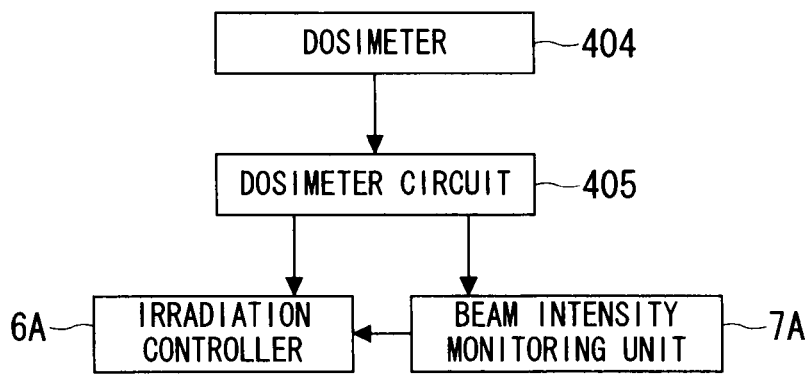
FIG. 14 is a functional block diagram relating to beam intensity monitoring in the laser-driven particle beam irradiation apparatus of FIG. 2.

FIG. 14 is a functional block diagram concerning the beam intensity monitoring in the laser-driven proton beam irradiation apparatus A, in which arrows represent a signal flow.

As like as the first embodiment, a dosimeter 404 of the irradiation port 4 outputs an electrical signal corresponding to the dose of the proton beam 104c that passed through the dosimeter 404, that is, the dose of the proton beam applied to the diseased site 9 of the patient. A dosimeter circuit 405 of the irradiation port 4 receives the electrical signal output from the dosimeter 404. When the received electrical signal reaches a preset integrated output value, the dosimeter circuit 405 sends a dose complete signal to the irradiation controller 6, indicating that the preset dose for the irradiation spot 902 set in the diseased site 9 of the patient has been reached.

The beam intensity monitoring unit 7A receives an electrical signal corresponding to the intensity of the proton beam per shot from the dosimeter circuit 405 and constantly matches the intensity of the proton beam indicated by the received electrical signal with a beam intensity 005 specified in the irradiation pattern data. When the intensity received from the dosimeter circuit 405 differs from the beam intensity specified in the irradiation pattern data by a predetermined value or greater, the beam intensity monitoring unit 7A sends an abnormal signal to the irradiation controller 6A.

The beam intensity 005 contained in the irradiation pattern data indicates the beam intensity under the conditions in which all the parameters and components such as the high-frequency electric filed for the energy distribution converging unit 5A and the energy separating magnet 301 of the energy selector 3 are properly adjusted. The beam intensity monitoring unit 7A determines, on the basis of the beam intensity in the irradiation pattern data, whether the beam intensity in a predetermined energy width around the energy peak formed in the energy distribution of laser-driven proton ray 103 (see FIG. 16) (peak intensity) is normal or not.

The laser-driven proton beam irradiation apparatus A will operate in the following manner.

It is herein assumed that in the irradiation pattern data, the energy corresponding to the range in patient 003 is 30 MeV and the energy width required for obtaining the beam stop position width in depth 004 is 5%.

In this case, the energy distribution convergence controller 604A of the irradiation controller 6A regulates the high-frequency voltage to be applied to the inner cavities 502A and regulates the high-frequency electric field applied to a proton beam 104d so that an energy peak is formed around 30 MeV in the energy distribution of the proton beam 104d.

The energy selection controller 602A of the irradiation controller 6A adjusts the energy separating magnet 301 and the position of the slit center C1 of the energy collimator 303 so that an energy width of 5% around the 30 MeV is extracted from the energy distribution of the proton beam 104d.

After the components 2, 3, 4, and 5A have been adjusted, the proton beam generator 1 generates laser-driven proton rays 103 and therapy radiation is performed on all radiation slices 901 set in the diseased site 9 of the patient according to the similar procedure to that of the first embodiment. If the intensity of the proton beam 104*c* applied to the diseased site 9 is not correct, the irradiation controller 6A stops the operation of the laser-driven proton beam irradiation apparatus A upon reception of an abnormal signal from the beam intensity monitoring unit 7A. The rest of the operation is the same as that of the laser-driven proton beam irradiation apparatus U of the first embodiment.

Hereunder, effects of the laser-driven proton beam irradiation apparatus A will be described.

Figure 15:
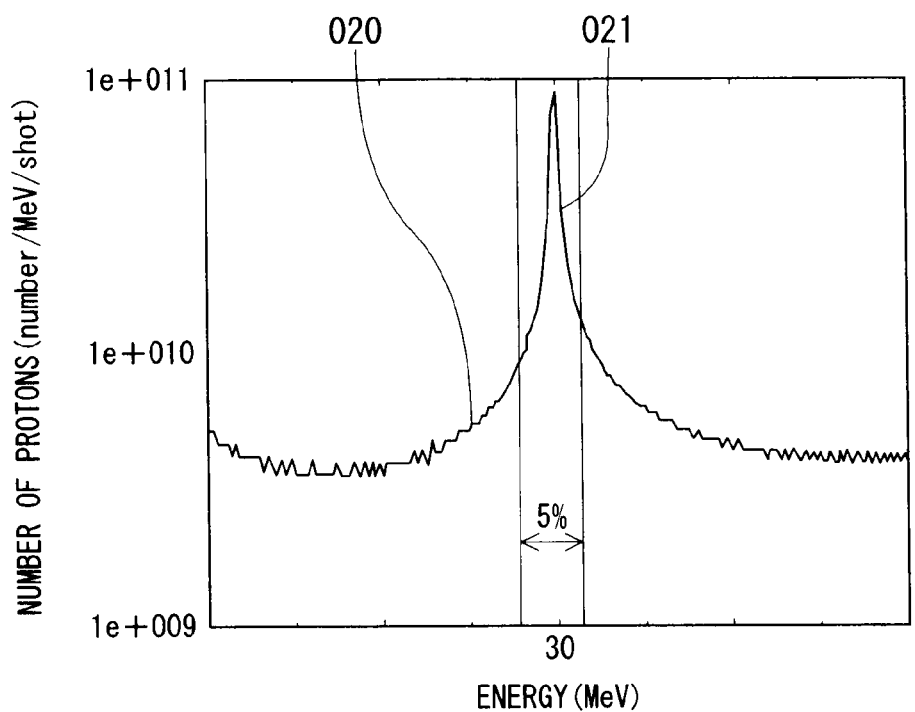
FIG. 15 is a diagram illustrating an energy distribution of a proton beam that passed through an energy distribution converging unit and an energy selector of the laser-driven particle beam irradiation apparatus of FIG. 2.
Figure 16:
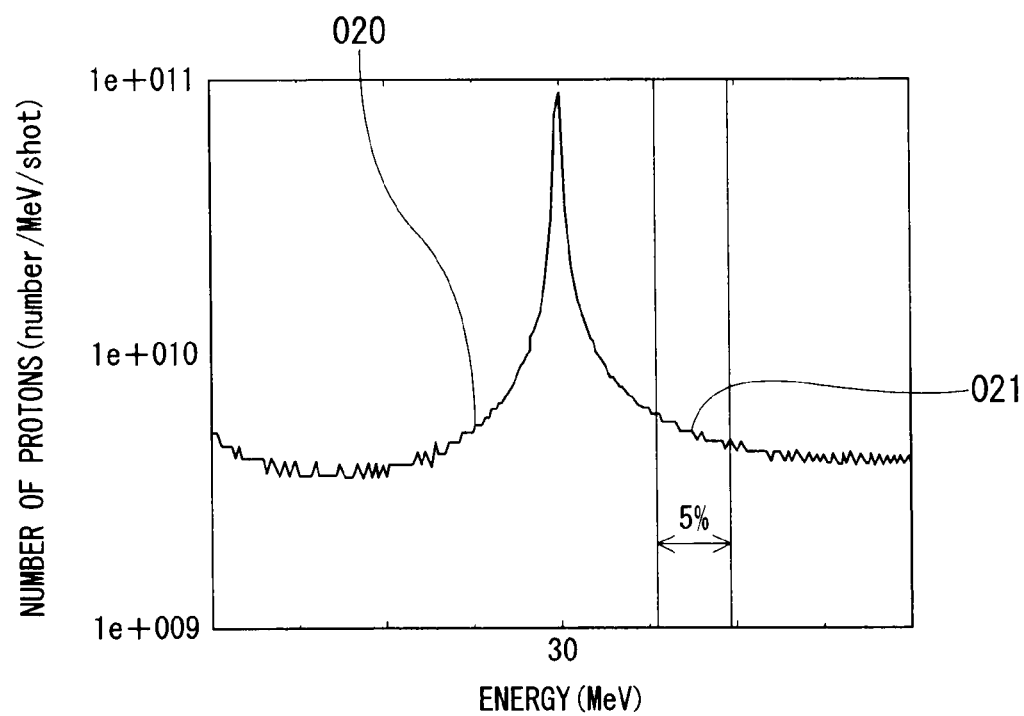
FIG. 16 is a diagram illustrating an energy distribution of a proton beam under abnormal conditions causing inaccurate energy selection of a proton beam in the laser-driven particle beam irradiation apparatus of FIG. 2.

FIGS. 15 and 16 are diagrams illustrating effects of the laser-driven proton beam irradiation apparatus A.

The compatibility between selection of energy and energy width of proton beam and intensity will be described.

FIG. 15 shows an energy distribution of a proton beam that passed through the energy distribution converging unit 5A and the energy selector 3 of the laser-driven proton beam irradiation apparatus A. In FIG. 15, the horizontal axis represents proton energy and the vertical axis represents the number of protons per shot of pulsed laser light 102. Reference numeral 020 represents the energy distribution of the proton beam after passing through the energy distribution converging unit 5A, and reference numeral 021 represents the energy distribution after passing through the energy selector 3.

In the laser-driven proton beam irradiation apparatus A, the energy of a proton beam 104*d* passing through the phase rotation cavity unit 500A of the energy distribution converging unit 5A energetically converges around the energy that appears when the timing at which the proton beam 104*d* passes through the gaps such as gap G2 between adjacent inner cavities 502A is in synchronization with the phase of the high-frequency voltage. For example, the energy of the proton beam converges around 30 MeV as shown in FIG. 15, and the percentage of protons having an energy of 30 MeV among the protons contained in the proton beam 104*d* increases.

Accordingly, if adjustment is made so that a proton beam with an energy of 30 MeV (±5%) passes through the slit S1 of the energy collimator 303 in the energy selector 3 as shown in FIG. 15, the intensity of the proton beam that passes through the slit S1 will become greater than that in the laser-driven proton beam irradiation apparatus U of the first embodiment.

Next, description on "Safety" will be made hereunder.

FIG. 16 shows an energy distribution of a proton beam under abnormal conditions in which inaccurate energy selection is made in the laser-driven proton beam irradiation apparatus A. In FIG. 16, the vertical and horizontal axes and the reference numerals represent the same parameters as those in FIG. 15.

Further, inaccurate energy selection is caused by a structural defect of the phase rotation cavity unit 500A of the energy distribution converging unit 5A or the energy collimator 303 of the energy selector 3, or by a control failure of the energy distribution convergence controller 604A or the energy selection controller 602.

An energy distribution of a proton beam that appears under abnormal conditions that caused inaccurate energy selection is significantly degraded as shown in FIG. 16 compared with the energy distribution of the proton beam that appears at the time of the correct energy selection. This is because before the proton beam reaches the slit S1 of the energy collimator 303 of the energy selector 3, the energy distribution of the proton beam is converged by the energy distribution converging unit 5A to increase the number of protons that have energy components that can pass through the slit S1.

Based on an electrical signal corresponding to the intensity of the proton beam having the energy distribution which has been converged through the energy distribution converging unit 5A, the beam intensity monitoring unit 7A determines whether abnormal selection has been made or not.

Therefore, the inaccurate energy selection can be reliably judged from a change in the intensity of the beam output from the dosimeter 404. That is, the inaccurate energy selection can be judged on the basis of the intensity of the proton beam in addition to the monitored exciting current of the energy separating magnet 301 in the energy selector 3 and the monitored position of the slit center C1 of the energy collimator 303 and the size of the slit S1.

In the laser-driven proton beam irradiation apparatus U according to the first embodiment, it is difficult to detect the inaccurate energy selection, if occurred, on the basis of the change in the intensity of the proton beam. This is because the energy distribution of the proton beam whose energy has not been converged by the energy distribution converging unit 5A is flat as shown in FIG. 12 (reference numeral 017) and, even if an energy slightly different from the desired energy is selected, the total intensity value of the proton beam that falls within a predetermined energy width does not significantly change. An abnormal signal may be output when a slight change in the intensity of a proton beam is detected. However, in that case, the interlock could be frequently activated because the proton beam energy selected by the energy selector 3 is usually slightly fluctuating.

The laser-driven proton beam irradiation apparatus A will attain the following advantageous functions and effects in addition to the advantageous effects (1) to (8) of the first embodiment.

(9) The laser-driven proton beam irradiation apparatus A includes the energy distribution converging unit 5A that forms the transportation path of the proton beam and converges the energy distribution of the proton beam in the transportation path to provide a peak at a particular energy. Therefore, the intensity of the proton beam that has the energy set on the basis of the depth of an irradiation spot 902 in a patient is increased and the advantageous effect described in (1) of the first embodiment is enhanced.

(10) The energy distribution converging unit 5A includes the phase rotation cavity unit 500A that forms the transportation path of the proton beam and, under the application of a high-frequency voltage, generates a high-frequency electric field in the transportation path where a state in which protons making up a proton bunch are accelerated and a state in which a protons making up a proton bunch are decelerated appear, thereby converging the energy distribution of the proton beam to a particular energy.

The irradiation controller 6A adjusts the phase and amplitude of the high-frequency voltage to be applied to the phase rotation cavity unit 500A to adjust the position of the energy peak of the energy distribution of the proton beam. Therefore, a desired energy peak can be formed in the energy distribution of the proton beam by using the charge and time-discrete states of the proton beam.

(11) The phase rotation cavity unit 500A of the energy distribution converging unit 5A includes the outer cavity 501A which forms the transportation path of a proton beam and inner cavities 502A which are spaced in a row inside the outer cavity 501A and to which a high-frequency voltage is applied. A high-frequency electric field is generated in the gaps between adjacent inner cavities 502A to converge the energy distribution of the proton beam around the energy of protons that enter the gaps at timing synchronizing with the phase of the high-frequency voltage applied to the inner cavities 502A among the protons making up a proton bunch in the outer cavity 501A. Therefore, the advantageous effect described in (10) can be readily and effectively achieved.

(12) The laser-driven proton beam irradiation apparatus A includes the beam intensity monitoring unit 7A that determines whether the intensity of the proton beam having the energy distribution which has been converged by the energy distribution converging unit 5A and having a particular energy has been selected by the energy selector 3, is normal or not. When the beam intensity monitoring unit 7A determines that the intensity is abnormal, the irradiation controller 6A stops irradiation of the diseased site 9 of the patient with the proton beam. Thus, an interlock using the intensity of a proton beam applied to the diseased site 9 can be provided, thereby further enhancing the safety of therapy radiation.

(13) The beam intensity monitoring unit 7A determines whether the intensity of the proton beam per shot of pulsed laser light 102 is normal or not. The beam intensity monitoring unit 7A makes the determination based on the peak intensity of the energy distribution of the proton beam. Accordingly, if the intensity of the proton beam deviates from a required value, the intensity of the proton beam provided to the dosimeter 404 is significantly decreased even though it is the intensity per shot. Therefore, whether the proton beam is normal or not can be determined with a high degree of accuracy. Accordingly the interlock can be activated with a high degree of reliability even during the irradiation of a single irradiation spot. Thus, the advantageous effect described in (12) can be enhanced.

Third Embodiment

A third embodiment concerns a high-frequency electric filed control for the proton beam performed in the laser-driven proton beam irradiation apparatus A of the second embodiment.

The irradiation controller 6A of the laser-driven proton beam irradiation apparatus A (see FIG. 10) applies a pulse width compressing voltage to the phase rotation cavity unit 500A by controlling the output of the high-frequency power supply 605A.

The pulse width compressing voltage is a voltage adjusted so as to compress the pulse width of proton rays contained in a proton beam 104d passing through the energy distribution converging unit 5A. The pulse width compressing voltage will be described below.

Hereunder, the description is given to the pulse width compressing voltage.

In the case of the phase rotation of the proton ray contained in the proton beam 104b about a given velocity, the velocity range in which the proton ray is phase-rotated can be expressed as:

[Equation 2]

$$\frac{\Delta v}{v_0} = \frac{v_0}{v_0 + fL} \tag{2}$$

where f is the frequency of the high-frequency voltage applied to inner cavities 502A of the phase rotation cavity unit 500A and L is the gap distance between the center of a target 101 generating the proton ray and the phase rotation cavity unit 500A.

By using the relationship $\Delta E/E_0 \approx \beta_0^2 \gamma_0^2 \cdot \Delta v/v_0$, Equation (2) will be rewritten as:

[Equation 3]

$$\frac{\Delta E}{E_0} = \beta_0^2 \gamma_0^2 \frac{v_0}{v_0 + fL} \tag{3}$$

wherein $\beta_0$ and $\gamma_0$ are Lorentz factors corresponding to $v_0$ and $E_0$ is the total energy including kinetic energy and rest energy corresponding to $v_0$.

By using the relationship $v_0 = c\sqrt{1 - m^2 c^4 / E_0^2}$, Equation (3) can be rewritten as:

[Equation 4]

$$\Delta E = E_0 \beta_0^2 \gamma_0^2 \frac{\sqrt{1 - m^2 c^4 / E_0^2}}{\sqrt{1 - m^2 c^4 / E_0^2} + fL/c} \tag{4}$$

wherein c is the speed of light and m is the mass of the particles.

To compress the pulse width $\Delta E$ of the proton ray by performing the phase rotation in the high-frequency electric field at the voltage (voltage amplitude) V, $\Delta E < qV$ needs to hold. Therefore, the voltage amplitude V of the pulse width compressing voltage can be expressed as:

[Equation 5]

$$V > \frac{E_0 \beta_0^2 \gamma_0^2}{q} \cdot \frac{\sqrt{1 - m^2 c^4 / E_0^2}}{\sqrt{1 - m^2 c^4 / E_0^2} + fL/c} \tag{5}$$

wherein q is the charge of the proton ray.

When the irradiation controller 6A adjusts the voltage to be applied to the phase rotation cavity unit 500A to a required pulse width compressing voltage, the irradiation controller 6A performs feedback control relating to the output of the high-frequency power supply 605A and, if the voltage value deviates from the required value, performs interlock stop control. This is because the voltage applied to the phase rotation cavity unit 500A tends to become unstable due to discharge or other causes.

The following functions and effects will be attained by the high-frequency electric field control for the proton beam according to the present embodiment.

Concerning the compression of pulse width of proton beam, the following explanation will be applied.

Figure 17A:
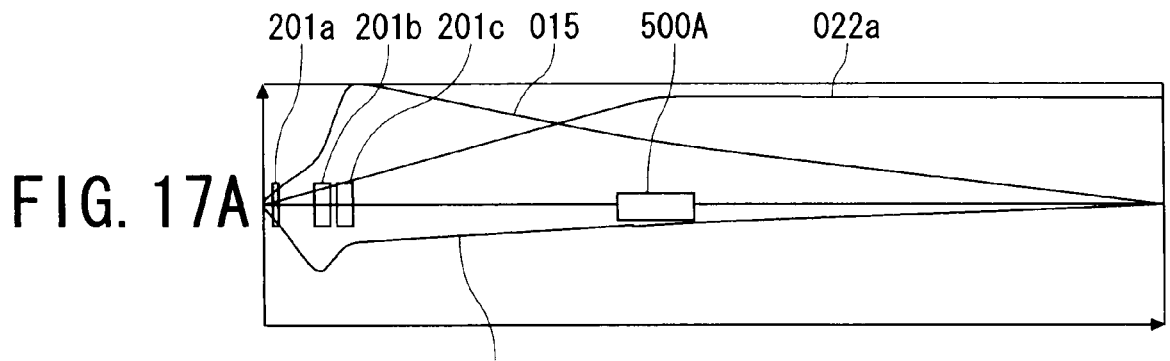
FIG. 17(A) illustrates the pulse width of a proton beam in the case where the voltage applied to a phase rotation cavity unit does not meet a pulse width compressing voltage value and FIG. 17(B) illustrates the pulse width of a proton beam in the case where the voltage applied to the phase rotation cavity unit meets the pulse width compressing voltage value.
Figure 17B:
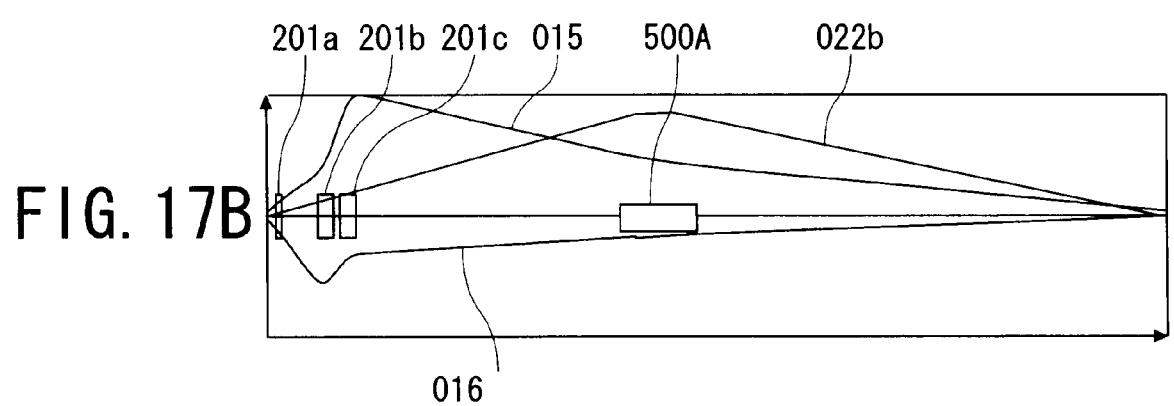

FIG. 17 represents a function of the high-frequency electric field control (results of simulations), in which FIG. 17A shows the pulse width of a proton beam in the case where the voltage applied to the phase rotation cavity unit 500A does not meet the condition (see Equation 5) for the pulse width compressing voltage, and FIG. 17B shows the pulse width of the proton beam in the case where the voltage applied to the phase rotation cavity unit 500A meet the condition (see Equation 5). Reference numeral 022a in FIG. 17A represents the pulse width of the proton beam not subjected to the pulse width compression, and reference numeral 022b in FIG. 17B represents the pulse width of the proton beam subjected to the pulse width compression. The vertical and horizontal axes and the other reference numerals in FIG. 17 are the same as those in FIG. 8.

In the laser-driven proton beam irradiation apparatus A, a laser-driven proton ray 103 emitted from the target 101 of the proton beam generator 1 has a certain pulse width. The pulse width of the laser-driven proton ray 103 increases as it travels through the energy selector 3 toward the diseased site 9 of the patient. For example, a pulse width of 1 nsec or less may increase to several nsec as shown in FIG. 17A.

In contrast, when the amplitude of the high-frequency voltage to be applied to the phase rotation cavity unit 500A of the energy distribution converging unit 5A is adjusted so as to satisfy condition (Equation 5), the pulse width of the proton beam 104d passing through the phase rotation cavity unit 500A is compressed and reduced. For example, a laser-driven proton ray 103 having a pulse width of 1 nsec or less emitted from the target 101 in the proton beam generator 1 travels through the energy selector 3, and consequently, the pulse width increases to 2.1 nsec. Then, the laser-driven proton ray 103 is subjected to the pulse width compression, and consequently, the pulse width is reduced to less than 1 nsec at the diseased site 9 of the patient as shown in FIG. 17B. Qualitatively, this is because the pulse of the proton beam 104d is compressed for the reason that slow proton rays contained in the proton beam 104b are accelerated and fast proton rays are decelerated. This is true for the energy distribution convergence function in the second embodiment.

The pulse width compression effect described above enables laser-driven proton rays 103 to be transported over a long distance while maintaining the original pulse width of the laser-driven proton rays 103. Practical benefits of the pulse width compression function or effect in proton radiation therapy will be described below.

Cancer cell killing actions of particle rays applied to the diseased site 9 of the patient can be broadly classified into two, direct and indirect, particle-cell interactions. The direct action is an interaction in which the particle ray directly damages or destroys DNA. On the other hand, in the indirect action, charges generated in the body of the patient by the particle ray generate active particles such as OH radicals and the interaction with the active particles damages or destroys DNA.

In general, when heavy particle rays such as carbon particle rays are used as particle rays in the therapy radiation, the direct action is dominant. For particle beams such as proton rays with low LET (linear energy transfer), the indirect action is dominant. The direct action has a higher cancer cell killing effect and can destroy cancer cells. Even if only a small number of OH radicals are generated as in hypoxic cells, the cancer cells can be destroyed by the direct action.

The pulse width compressing voltage compresses the pulse width of the proton beam to increase the density of proton rays. Consequently, in the pulse beam to which the pulse compression voltage is applied, the proportion of direct actions to the proton ray-cell interactions increases and therefore a radiation effect similar to that of heavy particle rays can be achieved. In addition, since the intensive energy can be applied in a short time, the effect of damaging/destroying cancer cell DNA can be enhanced by the heating effect.

The high-frequency electric field control for the proton beam according to the present embodiment has the following advantageous effects in addition to the effects (1) to (8) of the first embodiment and the effects (9) to (13) of the second embodiment.

(14) A pulse width compressing voltage that satisfies condition (Equation 5) is used to apply a high-frequency electric field to the phase rotation cavity unit 500A of the energy distribution converging unit 5A. Therefore, the density of the proton beam can be increased to increase its LET to a level comparable to those of heavy particle rays, thereby enhancing the effectiveness of therapy radiation.

Hereinabove, although the laser-driven particle beam irradiation apparatus and the laser-driven particle beam irradiation method according to the present invention have been described with respect to the first to third embodiments, the present invention is not limited to these embodiments and many other changes and modifications may be made without departing the spirits of the present invention defined in the appended claims.

For example, although the proton beam generator of laser-driven proton beam irradiation apparatus according to the embodiments irradiates a target with pulsed laser light to extract laser-driven proton rays, the particle rays to be extracted are not limited to proton rays, and any charged particles such as α rays or carbon rays may be extracted. In those cases, particle-dependant parameters in Equations (2) to (5) such as charge q and velocity $v_0$ in the third embodiment will be parameters relating to charged particle rays to be subjected to pulse width compression.

Furthermore, although the beam converging unit of the laser-driven proton beam irradiation apparatus in the examples described is configured with quadrupole magnets which are permanent magnets, the beam converging unit may be configured with hexapole or higher order multiple magnets.

Figure 18:
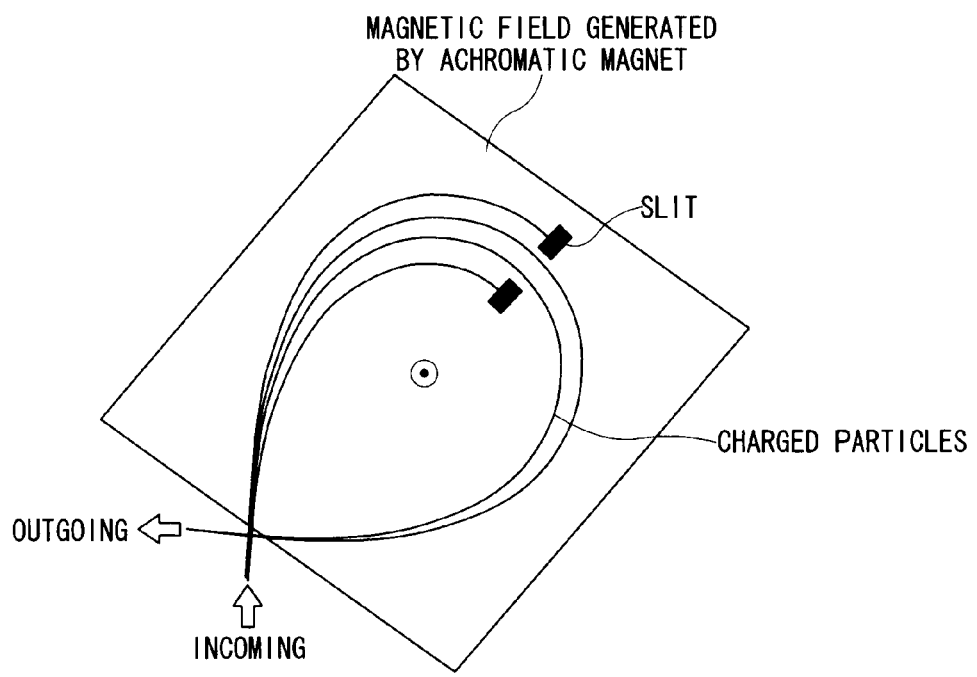
FIG. 18 is a diagram illustrating an exemplary of an arrangement for selecting an energy and energy width of charged particles using an achromatic magnet.

The function of the energy selector of the laser-driven proton beam irradiation apparatus that deflects the proton beam may be provide by an achromatic magnet (see FIG. 18) having an energy collimator provided therein. That is, the energy selector may be composed of any unit capable of: (i) guiding charged particles to a magnetic field, (ii) dispersing the trajectories of the charged particles by differences in momentum, (iii) selecting required charged particles (trajectories) after the trajectories have been dispersed in the magnetic field, and (iv) re-converging the trajectories when or after the charged particle exit the magnetic field.

The beam convergence controller and energy selection controller in the irradiation controller of the laser-driven proton beam irradiation apparatus refer to irradiation pattern data to adjust the positions of the quadrupole magnets of the beam converging unit, the exciting current for the energy selector, and the position of the slit of the energy collimator in the examples described. However, these adjustments may be performed based on adjustment quantities specified beforehand for each radiation slice.

A display device capable of displaying control variables such as the voltage to be applied to the phase rotation cavity unit (see Equation (1)) may be provided in the irradiation controller of the laser-driven particle beam irradiation apparatus to allow an operator to perform manual control or correction of the irradiation controller.

A laser-driven particle beam irradiation apparatus that is configured as follows enables therapy radiation using laser-driven particle rays and can increase the convergence of the laser-driven particle rays while reducing degradation of the intensity of the laser-driven particle rays in the course of transportation of the laser-driven particle rays to the diseased site of the patient.

Any laser-driven particle beam irradiation apparatus may be adopted as far as it comprises: a particle beam generator irradiating a target with pulsed laser light to emit a laser-driven particle ray; a beam converging unit forming a transportation path which guides the emitted laser-driven particle ray to an object to be irradiated and spatially converging the laser-driven particle ray; an energy selector selecting an energy and an energy width of the laser-driven particle ray; an irradiation port causing the laser-driven particle rays to scan the object to be irradiated to adjust a irradiation position in the object; and an irradiation controller controlling operation of the particle beam generator, the beam converging unit, the energy selector, and the irradiation port, wherein the beam converging unit generates a magnetic field on a trajectory of the laser-driven particle ray and converging the laser-driven particle ray by the magnetic field, the magnetic field forcing divergence components of the laser-driven particle ray that go away from the center of the trajectory back to the center of the trajectory.

What is claimed is:

1. A laser-driven particle beam irradiation apparatus comprising:
   a particle beam generator irradiating a target with pulsed laser light to emit a laser-driven particle ray;
   a beam converging unit forming a transportation path which guides the emitted laser-driven particle ray to an object to be irradiated and spatially converging the laser-driven particle ray;
   an energy selector selecting an energy and an energy width of the laser-driven particle ray;
   an irradiation port causing the laser-driven particle ray to scan the object to be irradiated to adjust an irradiation position in the object; and
   an irradiation controller controlling operation of the particle beam generator, the beam converging unit, the energy selector, and the irradiation port, wherein
   the beam converging unit generates a magnetic field on a trajectory of the laser-driven particle ray and converging the laser-driven particle ray by the magnetic field, the magnetic field forcing divergence components of the laser-driven particle ray that go away from a center of the trajectory back to the center of the trajectory, and
   the beam converging unit is provided between the particle beam generator and the energy selector.

2. A laser-driven particle beam irradiation apparatus comprising:
   a particle beam generator irradiating a target with pulsed laser light to emit a laser-driven particle ray;
   a beam converging unit forming a transportation path which guides the emitted laser-driven particle ray to an object to be irradiated and spatially converging the laser-driven particle ray;
   an energy selector selecting an energy and an energy width of the laser-driven particle ray;
   an irradiation port causing the laser-driven particle ray to scan the object to be irradiated to adjust an irradiation position in the object;
   an irradiation controller controlling operation of the particle beam generator, the beam converging unit, the energy selector, and the irradiation port; and
   an energy distribution converging unit forming the transportation path of the laser-driven particle ray and converging an energy distribution of the laser-driven particle ray through the transportation path to provide a peak at a particular energy, wherein
   the beam converging unit generates a magnetic field on a trajectory of the laser-driven particle ray and converging the laser-driven particle ray by the magnetic field, the magnetic field forcing divergence components of the laser-driven particle ray that go away from a center of the trajectory back to the center of the trajectory, and
   the energy distribution converging unit includes a phase rotation cavity unit forming a transportation path of the laser-driven particle ray and, under application of a high-frequency voltage, generating in the transportation path a high-frequency electric field in which a state in which protons in a bunch are accelerated and a state in which protons in a bunch are decelerated appear to converge the energy distribution of the laser-driven proton ray to a particular energy, and wherein the irradiation controller adjusts the phase of the high-frequency voltage to be applied to the phase rotation cavity unit to adjust the position of the energy peak of the energy distribution of the laser-driven particle ray.

3. The laser-driven particle beam irradiation apparatus according to claim 2, wherein the phase rotation cavity unit of the energy distribution converging unit includes an outer cavity forming the transportation path of the laser-driven particle ray and a plurality of inner cavities which are spaced in a row in the outer cavity and to which a high-frequency voltage is applied, wherein a high-frequency electric field is formed in a gap between adjacent inner cavities to converge the energy distribution of a proton beam around the energy of protons that enter the gap at a timing of being synchronized with the phase of the high-frequency voltage applied to the inner cavities among the protons in a bunch in the outer cavity.

4. The laser-driven particle beam irradiation apparatus according to claim 3, wherein the irradiation controller applies a pulse width compressing voltage to the inner cavities of the energy distribution converging unit to generate a high-frequency electric field in the gap between adjacent inner cavities, the pulse width compressing voltage being defined as $$V > \frac{E_0 \beta_0^2 \gamma_0^2}{q} \cdot \frac{\sqrt{1 - m^2 c^4 / E_0^2}}{\sqrt{1 - m^2 c^4 / E_0^2} + fL/c}$$

wherein f is the frequency of the high-frequency voltage to be applied to the inner cavities, L is the distance from a laser-driven particle ray emission point in the target to the gap between adjacent inner cavities, $\beta_0$ and $\gamma_0$ are Lorentz factors, $E_0$ is the total energy of the laser-driven particle ray, c is the speed of light, m is the mass of the laser-driven-particle ray, and q is the charge of the laser-driven particle ray.

5. A laser-driven particle beam irradiation method, comprising:
   a particle beam generating step of irradiating a target with pulsed laser light to extract a laser-driven particle ray;
   a beam converging step of spatially converging the laser-driven particle ray;
   an energy selecting step of selecting an energy and an energy width of the laser-driven particle ray according to a depth of an irradiation position set in an object to be irradiated;
   an irradiation step of adjusting the irradiation position of the laser-driven particle ray in the object to be irradiated; and
   a pulse width compressing step of reducing the pulse width of the laser-driven particle ray,
   wherein, in the beam converging step, a magnetic field forcing divergence components of the laser-driven particle ray that go away from a center of the trajectory of the laser-driven particle ray back to the center of the trajectory is generated on the trajectory and the laser-driven particle ray is converged by the magnetic field.

6. The laser-driven particle beam irradiation method according to claim 5, wherein, in the pulse width compressing step, a high-frequency electric field induced by a pulse width compressing voltage is generated and the laser-driven particle ray is guided to and passed through the high-frequency electric field to reduce the pulse width of the laser-driven particle ray, the pulse width compressing voltage being defined as $$V > \frac{E_0 \beta_0^2 \gamma_0^2}{q} \cdot \frac{\sqrt{1 - m^2 c^4 / E_0^2}}{\sqrt{1 - m^2 c^4 / E_0^2} + fL/c}$$

wherein f is the frequency of the high-frequency voltage, L is the distance from a laser-driven particle ray emission point, $\beta_0$ and $\gamma_0$ are Lorentz factors, $E_0$ is the total energy of the laser-driven particle ray, c is the speed of light, m is the mass of the laser-driven-particle ray, and q is the charge of the laser-driven particle ray.

* * * * *